United States Patent [19]

Dellaria et al.

[11] Patent Number: 5,516,795
[45] Date of Patent: May 14, 1996

[54] HETEROATOM SUBSTITUTED PROPANYL DERIVATIVES HAVING 5-LIPOXYGENASE INHIBITORY ACTIVITY

[75] Inventors: Joseph F. Dellaria, Lindenhurst; Linda J. Chernesky, Arlington Heights, both of Ill.

[73] Assignee: Abbott Laboratories, Abbott Park, Ill.

[21] Appl. No.: 304,745

[22] Filed: Sep. 12, 1994

[51] Int. Cl.⁶ .................... A61K 31/335; C07D 317/26
[52] U.S. Cl. ............................. 514/467; 549/452
[58] Field of Search .................... 549/451, 452; 548/317; 546/226, 207; 544/384, 380, 374, 169, 161, 159, 148; 514/467

*Primary Examiner*—Nicky Chan
*Attorney, Agent, or Firm*—Jerry F. Janssen

[57] ABSTRACT

Compounds of the structure

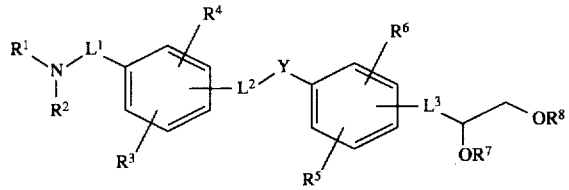

where $R^1$ is alkyl of one to four carbon atoms and $R^2$ is selected from (a) alkenyl of one to four carbon atoms, (b)

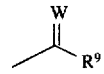

(c)

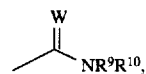

and (d)

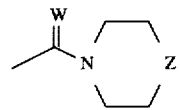

are potent inhibitors of lipoxygenase enzymes and thus inhibit the biosynthesis of leukotrienes. These compounds are useful in the treatment or amelioration of allergic and inflammatory disease states.

10 Claims, No Drawings

HETEROATOM SUBSTITUTED PROPANYL DERIVATIVES HAVING 5-LIPOXYGENASE INHIBITORY ACTIVITY

TECHNICAL FIELD

This invention relates to compounds having biological activity to inhibit lipoxygenase enzymes, to pharmaceutical compositions comprising these compounds, and to a medical method of treatment. More particularly, this invention concerns certain heteroatom substituted propanyl compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis, cis-1,4-pentadiene structures, convening them to 1-hydropcroxy-trans, cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or convened to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a as number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5lipoxygenase are thus useful in the treatment of disease states such as those listed above in which the leukotrienes play an important role.

SUMMARY OF THE INVENTION

In its principal embodiment, the present invention provides certain heteroatom substituted propanyl compounds which inhibit lipoxygenase enzyme activity and are useful in the treatment of allergic and inflammatory disease states in which leukotrienes play a role.

The compounds of this invention and their pharmaceutically acceptable salts have the structure

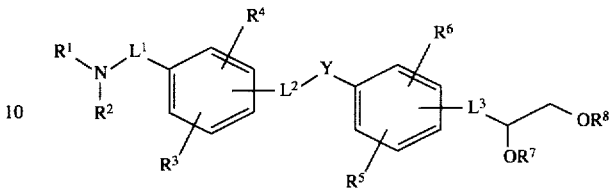

where $L^1$ and $L^2$ are independently a single bond or are independently selected from the group consisting of alkylene of one to three carbon atoms, propenylene, and propynylene.

$L^3$ is selected from the group consisting of (a)

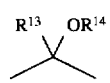

and (b)

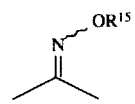

where $R^{13}$ is hydrogen or alkyl of one to four carbon atoms, $R^{14}$ is alkyl of one to four carbon atoms, and $R^{15}$ is hydrogen or alkyl of one to four carbon atoms.

Y is selected from oxygen, $>NR^{12}$ where $R^{12}$ is hydrogen or alkyl of one to four carbon atoms, and $>S(O)_n$ where n= 0, 1, or 2.

$R^1$ is alkyl of one to four carbon atoms; and $R^2$ is selected from the group consisting of (a) alkenyl of one to four carbon atoms, (b)

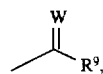

(c)

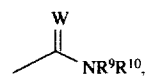

and (d)

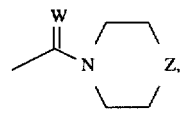

where W is oxygen or sulfur, Z is —$CH_2$—, oxygen, sulfur, or —$NR^{11}$ wherein $R^{11}$ is hydrogen or alkyl of one to four carbon atoms. $R^9$ is alkyl of one to four carbon atoms, or $R^1$ and $R^9$, together with the nitrogen atoms to which they are attached, define a ring selected from the group consisting of

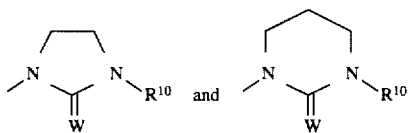

where $R^{10}$ is selected from the group consisting of (a) hydrogen, (b) alkyl of one to four carbon atoms, (c) haloalkyl of one to four carbon atoms, (d) cyanoalkyl of one to four carbon atoms, (e) unsubstituted phenyl, (f) phenyl substituted with a substituent selected from the group consisting of alkyl of one to four carbon atoms, alkoxy of one to four carbon atoms, haloalkyl, of one to six carbon atoms, and halogen, (g) hydroxyalkyl of one to four carbon atoms, (h) aminoalkyl of one to four carbon atoms, (i) carboxyalkyl of one to four carbon atoms, (j) (alkoxycarbonyl)alkyl where the alkyl and alkoxy portions each are of one to four carbon atoms, and (k) (alkylaminocarbonyl)alkyl, where the alkyl portions are independently of one to four carbon atoms.

$R^3$, $R^4$, $R^5$, and $R^6$ are independently selected from the group consisting of hydrogen, alkyl of one to four carbon atoms, alkoxy of one to four carbon atoms, haloalkyl of one to four carbon atoms, halogen, cyano, amino, alkoxycarbonyl of one to four carbon atoms, and dialkylaminocarbonyl where the alkyl portions are each of one to four carbon atoms.

$R^7$ and $R^8$ are alkyl of one to four carbon atoms, or taken together with the oxygen atoms to which they are attached and the carbon atoms to which the oxygen atoms in turn are attached, form a ring of the structure where $R^{16}$ and $R^{17}$ are independently selected from the group consisting of hydrogen, alkyl of one to four carbon atoms, alkoxy of one to four carbon atoms, and haloalkyl of one to four carbon atoms.

In another embodiment, the present invention provides pharmaceutical compositions which comprise a therapeutically effective amount of compound as defined above in combination with a pharmaceutically acceptable carder.

In yet another embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION OF THE INVENTION

Definitions of Terms

As used throughout this specification and the appended claims, the term is "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the structure —NHR' wherein R' is alkyl as previously defined. Example of alkylamino include methylamino, ethylamino, iso-propylamino, and the like.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, isopropylaminocarbonyl, and the like.

The term "alkanoyl" refers to an alkyl group, as defined above, attached to the parent molecular moiety through a carbonyl group. Alkanoyl groups are exemplified by formyl, acetyl, butanoyl, and the like.

The term "propanyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, as two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxycarbonyl" represents an ester group; i.e. an alkoxy group attached to the parent molecular moiety through a carbonyl group. Representative alkoxycarbonyl groups include methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl- 2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2dimethylpropylene, and the like.

The term "aminoalkyl" denotes an —$NH_2$ group attached to the parent molecular moiety through an alkylene group. Representative aminoalkyl groups include 2-amino-1-ethylene, 3-amino-1-propylene, 2-amino-1-propylene, and the like.

The term "carboxyalkyl" denotes a —$CO_2H$ group attached to the parent molecular moiety through an alkylene group. Representative carboxyalkyl groups include, 1-carboxyethyl, 2-carboxyethyl, 1-carboxypropyl, and the like.

The term "(alkoxycarbonyl)alkyl" denotes an alkoxycarbonyl group, as defined above, attached to the parent molecular moiety through an alkylene group. Representative (alkoxycarbonyl)alkyl groups include ethoxycarbonylmethyl, ethoxycarbonylethyl, methoxycarbonylpropyl, and the like.

The term "(alkylaminocarbonyl)alkyl" denotes an alkylaminocarbonyl group, as defined above, attached to the parent molecular moiety through an alkylene group. Examples of (alkylaminocarbonyl)alkyl groups include methylaminocarbonylmethyl, methylaminocarbonylpropyl, isopropylaminocarbonylmethyl, and the like.

The term "alkenylene" denotes a divalent group derived from a straight or branched chain hydrocarbon containing at least one carbon-carbon double bond. Examples of alkenylene include —CH=CH—, —$CH_2$CH=CH—, —C($CH_3$)=CH—, —$CH_2$CH=CH$CH_2$—, and the like.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk milo. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laumte, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerote salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetmethylammonium, methylamine, dimethylamine, trimethylamine, triethylamine, ethylamine, and the like.

PREFERRED EMBODIMENTS

Compounds contemplated as falling withing the scope of the present invention include, but are not limited to:

E-(4S )-O-methyl-2,2-dimethyl-4-[(5-fluoro-3-(4-(N', N'-dimethylaminocarbonyl-N-methylamino)benzyloxy)phenyl)oximinomethyl] -1,3-dioxolane, E-(4S)-O-methyl-2,2-dimethyl-4-[(5-fluoro-3-(4 -(N-acetyl-N-methylamino)benzyloxy)phenyl)oximinomethyl] -1,3-dioxolane, Z-(4S)-O-methyl-2,2-dimethyl-4-[(3 -(4-(N-allyl-N-methylamino)phenylthioxyl)phenyl)oximinomethyl] -1,3-dioxolane, E-(4S)-O-methyl-2,2-dimethyl-4-[(3 -(4-(N-allyl-N-methylamino)phenylthioxyl)phenyl)oximinomethyl] -1,3-dioxolane, Z-(4S )-O-methyl-2,2-dimethyl-4-[ (3-(4-(N', N'-dimethylaminocarbonyl-N-methylamino)phenylthioxyl)phenyl)oximinomethyl] -13-dioxolane, E-(4S )-O-methyl-2,2-dimethyl-4-[ (3-(4-(N', N'-dimethylaminocarbonyl-N-methylamino)phenylthioxyl)phenyl)oximinomethyl] -1,3-dioxolane, Z-(4R )-O-methyl-2,2-dimethyl-4-[(3 -(4-(N-allyl-N-methylamino)phenylthioxyl)phenyl)oximinomethyl] -1,3-dioxolane, E-(4R)-O-methyl-2,2-dimethyl-4-[(3-(4-(N-allyl-N-methylamino)phenylthioxyl)phenyl)oximinomethyl] -13-dioxolane, Z-(4R )-O-methyl-2,2-dimethyl-4-[ (5-fluoro-3-(4-(N', N'-dimethylaminocarbonyl-N-methylamino)phenylthioxyl} phenyl)oximinomethyl]-1,3-dioxolane, E-(4R )-O-methyl-2,2-dimethyl-4-[(5- fluoro-3-(4 -(N', N'-dimethylaminocarbonyl-N-methylamino)phenylthioxyl} phenyl)oximinomethyl]-13-dioxolane, Z-(4R )-O-methyl- 2,2-dimethyl-4-[ (5- fluoro-3-(4 -(N', N'-dimethylaminocarbonyl-N-methylamino)benzyloxy)phenyl)oximinomethyl] -13-dioxolane, E-(4R)-O-methyl-2,2-dimethyl-4-[(5-fluoro-3-(4 -(N', N'-dimethylaminocarbonyl-N-methylamino)benzyloxy)phenyl)oximinomethyl] -13-dioxolane, Z-(4S )-2,2-dimethyl-4-[(3 -(4-(N-allyl-N-methylamino)phenylthioxyl)phenyl)oximinomethyl] -13-dioxolane, E-(4S)-2,2-dimethyl-4-[ (3-(4 -(N-allyl-N-methylamino)phenylthioxyl)phenyl)oximinomethyl] -1,3-dioxolane, Z-(4S)-O-methyl-2,2-dimethyl-4-[(3 -(4-(N-allyl-N-methylamino)phenylsulfinyl)phenyl)oximinomethyl] -13-dioxolane, E-(4S)-O-methyl-2,2-dimethyl-4-[(3 -(4-(N-allyl-N-methylamino)phenylsulfinyl)phenyl)oximinomethyl] -1,3-dioxolane, Z-(4S)-O-methyl-2,2-dimethyl-4-[(3 -(4-(N-allyl-N-methylamino)phenylsulfonyl)phenyl)oximinomethyl] -13-dioxolane, E-(4S )-O-methyl-2,2-dimethyl-4-[ (3 -(4-(N-allyl-N-methylamino)phenylsulfonyl)phenyl)oximinomethyl] -13-dioxolane, Z-(4S ) -O-methyl-2,2-dimethyl-4-[(3-(4 -(N', N'-dimethyl aminothiocarbonyl-N-methylamino)phenylthioxyl)phenyl)oximinomethyl] -13-dioxolane, E-(4S)-O-methyl-2,2-dimethyl-4-[(3 -(4-(N',N'-dimethylaminothiocarbonyl-N-methylamino)phenylthioxyl)phenyl)oximinomethyl] -1,3-dioxolane, Z-(4S)-O-methyl-2,2-dimethyl-4-[(5-fluoro-3 -(4-((N', N'-dimethylaminocarbonyl)-N-methylamino)benzylthioxy)phenyl)oximinomethyl] -13-dioxolane, E-(4S)-O-methyl-2,2-dimethyl-4-[ (5-fluoro-3-(4 -(N', N'-dimethylaminocarbonyl-N-methylamino)benzylthioxy)phenyl)oximinomethyl] -13-dioxolane, anti-(1 S, 2R)- 1-[(5-fluoro3-(4 -(N',N'-dimethylaminocarbonyl-N-methylamino)benzyloxy)phenyl) ]-1,2,3-trimethoxypropane, anti-(1S, 2R)-1-[(5-fluoro-3-{4-(N-acetyl-N-methylamino)benzyloxy)phenyl)]- 1,2,3 -trimethoxypropane, anti-(1S, 2R)-1-[3-(4-(N-allyl-N-methylamino)phenylthioxyl)phenyl]-1,2,3-trimethoxypropane, anti-(1S, 2R)- 1-[3 -(4-(N', N'-dimethylaminocarbonyl-N-methylamino)phenylthioxyl)phenyl] -1,2,3-trimethoxypropane, anti-(1S, 2R)-1-[5-fluoro-3 -(4-(N', N'-dimethylaminocarbonyl-N-methylamino)benzylthioxyl)phenyl] -1,2,3-trimethoxypropane, Z-(4S)-O-methyl-2,2-dimethyl-4-[ (5-fluoro-3 -((4-(N', N'-dimethylaminocarbonyl-N-methylamino)methyl)benzyloxy)phenyl)oximinomethyl] -13-dioxolane, E-(4S)-O-methyl-2,2-dimethyl-4-[ (5-fluoro-3-((4 -(N', N'-dimethylaminocarbonyl-N-methylamino)methyl)benzyloxy)phenyl)oximinomethyl] -1,3-dioxolane, Z-(4S)-O-methyl-2,2-dimethyl-4-[(5-fluoro-3 -(4-(imidazolidin-2-on-1-ylmethyl)benzyloxy)phenyl)oximinomethyl] -1,3-dioxolane, E-(4S)-O-methyl-2,2-dimethyl-4-[ (5-fluoro-3 -(4-(imidazolidin-2-on-1-ylmethyl)benzyloxy)phenyl)oximinomethyl] -1,3-dioxolane, Z- (1S)-O-methyl-4-[(3 -(4-(N-allyl-N-methylamino)phenylthioxyl)phenyl)oximinomethyl] ]-1,2-dimethoxyethane, E-(1S)-O-methyl-4-[(3 -(4-(N-allyl-N-methylamino)phenylthioxyl)phenyl)oximinomethyl] ]-1,2-dimethoxyethane, Z-(1S)-O-methyl-4-[(3-(4 -(N',N'-dimethylaminocarbonyl-N-methylamino)phenylthioxyl)phenyl)oximinomethyl] -1,2-dimethoxyethane, E-(1S)-O-methyl-4-[(3-(4 -(N',N'-dimethylaminocarbonyl-N-methylamino)phenylthioxyl)phenyl)oximinomethyl] -1,2-dimethoxyethane, E-(1S)-O-methyl-4- [(3-(4 -(N', N'-dimethylaminocarbonyl-N-methylamino)phenylthioxyl)phenyl)oximinomethyl] -1,2-dimethoxyethane, Z-(1S)-O-methyl-4-[(3-(4 -(N',N'-dimethylaminocarbonyl-N-methylamino)phenylthioxyl)phenyl)oximinomethyl] -1,2-dimethoxyethane, E-(4S)-O-methyl-2,2-dimethyl-4-[(3-(4-(N-acetyl-N-methylamino)phenylthioxyl)phenyl)oximinomethyl]-1,3-dioxolane, Z-(4S)-O-methyl-2,2-dimethyl-4-[(3-(4-(N-acetyl-N-methylamino) phenylthioxyl)phenyl)oximinomethyl]-1,3-dioxolane, E-(4S)-O-methyl-2,2-dimethyl-4-[(5-fluoro-3-(4-(N-allyl-N-methylamino)phenylthioxyl)phenyl)oximinomethyl]-1,3-dioxolane, Z-(4S)-O-methyl-2,2-dimethyl-4-[(5-fluoro-3-(4-(N-allyl-N-methylamino) phenylthioxyl)phenyl)oximinomethyl]-13-dioxolane, E-(4S)-O-methyl-2,2-dimethyl-4-[(5-fluoro-3-(4-(N',N'-dimethylaminocarbonyl-N-methylamino) thioxyl)phenyl)oximinomethyl]-13-dioxolane, Z-(4S)-O-methyl-2,2-dimethyl-4-[(5-fluoro-3-(4-(N',N'-dimethylaminocarbonyl-N-methylamino) phenylthioxyl)phenyl)oximinomethyl]-1,3-dioxolane, anti-(1S, 2R)-1-[5-fluoro-3 -(4-(N-allyl-N-methylamino)phenylthioxyl)phenyl]- 1,2,3-trimethoxypropane, anti-(1S, 2R)- 1-[5-fluoro-3 -(4-(N', N'-dimethylaminocarbonyl-N-methylamino)phenylthioxyl)phenyl] -1,23-trimethoxypropane, E-(4S)-O-methyl-2,2-dimethyl-4-[(3-(4-(N-(4-methylpipemzin-1-ylcarbonyl)-N-methylamino) phenylthioxyl)phenyl)oximinomethyl]-13-dioxolane, Z-(4S)-O-methyl-2,2-dimethyl-4-[(3-(4-(N-(4-methylpipemzin-1 -ylcarbonyl)-N-methylamino)phenylthioxyl)phenyl)oximinomethyl]-dioxlane, anti-(1S, 2R)-1-[3-(4 -(N-(4-methylpipemzin-1-ylcarbonyl)-N-methylamino)phenylthioxyl)phenyl] -1,2,3-trimethoxypropane, E-(4S)-O-methyl-2,2-dimethyl-4-[(5-fluoro-3-(4 -(N'-methyl-N'-(3-aminoprop-1-yl)aminocarbonyl-N-methylamino)benzyloxy)phenyl)oximinomethyl] -13dioxolane, Z-(4S)-O-methyl-2,2-dimethyl-4-[(5-fluoro-3-(4-(N'-methyl-N'-(3-aminoprop-1-yl) aminocarbonyl-N-methylamino)benzyloxy)phenyl)oximinomethyl]-1,3-dioxolane, E-(4S)-O-methyl-2,2-dimethyl-4-[(5-fluoro-3-(4-(N'-methyl-N' -(4-hydroxybut- 1-yl)aminocarbonyl-N-methylamino)benzyloxy)phenyl)oximinomethyl] -13dioxolane, Z-(4S)-O-methyl-2,2-dimethyl-4-[(5-fluoro-3-(4-(N'-methyl-N' -(4-hydroxybut-1-yl)aminocarbonyl-N-methylamino)benzyloxy)phenyl)oximinomethyl] -1,3-dioxolane, E-(4S)-O-methyl-2,2-dimethyl-4-[ (5-fluoro-3-(4-(N'-methyl-N'-(3-carboxyprop-1-yl) aminocarbonyl-N-methylamino)benzyloxy)phenyl)oximinomethyl]-1,3-dioxolane, Z-(4S)-O-methyl-2,2-dimethyl-4-[ (5-fluoro-3-(4-(N'-methyl-N'-(3-carboxyprop-1-yl) aminocarbonyl-N-methylamino)benzyloxy)phenyl)oximinomethyl]-1,3dioxolane, E-(4S)-0-methyl-2,2-dimethyl-4-[(5-fluoro-3-(4 -(N'-methyl-N'-(3-ethoxycarbonylprop- 1-yl)aminocarbonyl-N-methylamino)benzyloxy)phenyl)oximinomethyl] -1,3-dioxolane, Z-(4S)-O-methyl-2,2-dimethyl-4-[(5-fluoro-3 -(4-(N'-methyl-N'-(N"-ethoxycarbonylprop-1-yl)aminocarbonyl-N-methylamino)benzyloxy)phenyl)oximinomethyl] -1,3-dioxolane, E-(4S)-O-methyl-2,2-dimethyl-4-[(5-fluoro-3-(4-(N'-methyl-N' -(N"-methylaminocarbonylprop-1-yl)aminocarbonyl-N-methylamino)benzyloxy)phenyl)oximinomethyl] -1,3-dioxolane, Z-(4S)-O-methyl-2,2-dimethyl-4-[(5-fluoro-3-(4 -(N'-methyl-N'-(N"-methylaminocarbonylprop- 1-yl)aminocarbonyl-N-methylamino)benzyloxy)phenyl)oximinomethyl] -1,3-dioxolane, anti-(1S, 2R)-1-[(5-fluoro-3-(4-(N'-methyl-N'-(3-aminoprop-1-yl)aminocarbonyl-N-methylamino)benzyloxy) phenyl)]-1,2,3-trimethoxypropane, anti-(1S, 2R)- 1-[(5-fluoro-3 -(4-(N'-methyl-N'-(4-hydroxybut-1-ylaminocarbonyl-N-methylamino) benzyloxy)phenyl)]- 1,2,3-trimethoxypropane, anti-(1S, 2R)-1-[(5-fluoro-3-(4-(N'-methyl-N'-(3 -carboxyprop-1-yl)aminocarbonyl-N-methylamino)benzyloxy)phenyl)] -1,2,3-trimethoxypropane, anti-(1S, 2R)-1-[(5-fluoro-3-(4-(N'-methyl-N' -(3-ethoxycarbonylprop-1-yl)aminocarbonyl-N-methylamino)benzyloxy)phenyl)] -1,2,3trimethoxypropane, and anti-(1S, 2R)-1-[(5-fluoro-3-(4-(N'-methyl-N' -(N "-methylaminocarbonylprop-1-yl)aminocarbonyl-N-methylamino)benzyloxy)phenyl)] -1,2,3-trimethoxypropane.

Preferred compounds of the present invention have the structure defined above wherein $R^1$ is alkyl of one to four carbon atoms; $R^2$ is selected from (a) alkenyl of one to four carbon atoms, (b)

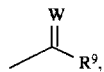

and (c)

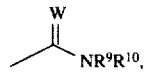

where W is oxygen, $R^9$ is alkyl of one to four carbon atoms, and $R^{10}$ is alkyl of one to four carbon atoms; $L^1$ is a valence bond; $L^2$ is a valence bond or alkyl of one to four carbon atoms; $L^3$ is selected from (a)

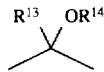

where $R^{13}$ is hydrogen and $R^{14}$ is alkyl of one to four carbon atoms, and (b)

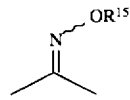

where $R^{15}$ is hydrogen or alkyl of one to four carbon atoms; $R^7$ and $R^8$ are alkyl of one to four carbon atoms, or taken together define a group of formula

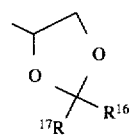

where $R^{16}$ and $R^{17}$ are independently selected from hydrogen and alkyl of one to four carbon atoms; Y is selected from oxygen and >S(O)n where n= 0, 1, or 2; and $R^3$, $R^4$, $R^5$, and $R^6$ are as defined above.

Particularly preferred compounds of the present invention have the structure defined immediately above wherein $L^2$ is a valence bond and Y is S. Examples include:

E-(4S)-O-methyl-2,2-dimethyl-4-[(5-fluoro-3 -(4-(N',N'-dimethylaminocarbonyl-N-methylamino)benzyloxy)phenyl)oximinomethyl] -1,3dioxolane, E-(4S  )-O-methyl-2,2-dimethyl-4-[(5-fluoro-3-(4-(N-acetyl-N-methylamino)benzyloxy)phenyl)  -1,3-dioxolane, and E-(4S )-O-methyl-2,2-dimethyl-4-[(3-(4-(N-allyl-N-methylamino)phenylthioxyl)phenyl)oximinomethyl]-1,3-dioxolane.

The most preferred compounds of the present invention are:

Z-(4S )-O-methyl-2,2-dimethyl-4-[ (3-(4-(N-allyl-N-methylamino)phenylthioxyl)phenyl)oximinomethyl] -13-dioxolane, E-(4S )-O-methyl-2,2-dimethyl-4-[ (3-(4-(N-allyl-N-methylamino)phenylthioxyl)phenyl)oximinomethyl] -13-dioxolane, Z-(4S)-O-methyl-2,2-dimethyl-4-[(3-(4 -(N', N'-dimethylaminocarbonyl-N-methylamino)phenylthioxyl)phenyl)oximinomethyl] -13-dioxolane, E-(4S)-O-methyl-2,2-dimethyl-4-[ (3 -(4-(N', N'-dimethylaminocarbonyl-N-methylamino)phenylthioxyl)phenyl)oximinomethyl] -1,3-dioxolane, E-(4R)-O-methyl-2,2-dimethyl-4-[(5-fluoro-3-(4   -(N', N'-dimethylaminocarbonyl-N-methylamino)benzyloxy)phenyl)oximinomethyl] -13-dioxolane, anti-(1S, 2R)-1-[(5-fluoro-3-(4 -(N',N'-dimethylaminocarbonyl-N-methylamino)benzyloxy)phenyl)]   -1,2,3-trimethoxypropane, and anti-(1S,  2R)-1-[(5-fluoro-3-{   4-(N-acetyl-N-methylamino)-benzyloxy)phenyl)] -1,2,3-trimethoxypropane.

Certain compounds of this invention may exist in either cis or trans or E or Z isomers with respect to the oxime geometry and in addition to stereoisomeric forms by virtue of the presence of one or more chiral centers. The present invention contemplates all such geometric and stereoisomers, including R- and S-enantiomers, diastereomers, and cis/trans or E/Z mixtures thereof as falling within the scope of the invention. If a particular enantiomer is desired, it may be prepared by asymmetric synthesis or by derivatization with a chiral auxiliary and the resulting diastereomeric mixture is separated and the auxiliary group cleaved to provide the pure desired enantiomers.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 µM) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated in Table 1.

TABLE 1

| In Vitro Inhibitory Potencies of Compounds of this Invention Against 5-Lipoxygenase from Stimulated $LTB_4$ Formation in Human Whole Blood | |
|---|---|
| Example | $IC_{50}$ ($10^{-6}$ M) |
| 1 | 100% @ 0.100 µM |
| 2 | 82% @ 0.20 µM |
| 3 | 99% @ 6.25 µM |
| (Z oxime) | |
| 3 | 0.05 |

TABLE 1-continued

| In Vitro Inhibitory Potencies of Compounds of this Invention Against 5-Lipoxygenase from Stimulated $LTB_4$ Formation in Human Whole Blood | |
|---|---|
| Example | $IC_{50}$ ($10^{-6}$ M) |
| (E oxime) | |
| 4 | 100% @ 6.25 µM |
| 5 | 100% @ 0.78 µM |
| 14 | 49% @ 0.10 µM |
| 15 | 42% @ 0.78 µM |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to s humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use a liquid suspension of crystalline or amorphous material with poor water solubility. The rate of absorption of the drug then depends upon its s rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carder such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl as formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable nonirritating excipients or carders such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are as administered orally to a mammalian patient. If desired, the effective daily dose may be divided into multiple doses for purposes of administration, e.g. two to four separate doses per day.

Preparation of the Compounds of the Invention

The compounds of this invention may be prepared by a variety of synthetic routes. Representative procedures are outlined as follows. It should be understood that $L^1$, $L^2$, $R^1$, $R^2$, $R^3$, $R^4$, $R^7$, $R^{13}$, $R^{14}$, $R^{15}$, and $R^{16}$ as used herein, correspond to the groups identified above.

The preparation of trialkoxypropane derivatives is shown in Scheme 1. Aryl bromide 1, prepared according to the method described in EPA 385 679, is metallated using, for example, n-butyllithium, in an organic solvent such as THF. Addition of 2,2-dimethyl-1,3-dioxolane to the aryllithium provides alcohol 2 which is converted to ether 3 by reaction with NaH and $R^{13}X$, where $R^{13}$ is defined above and X is a suitable leaving group such as Cl, Br, I, methanesulfonyl, or p-toluenesulfonyl. Hydrolysis of the dioxane by treatment with catalytic p-toluenesulfonic acid in methanol affords diol 4 which is converted to trialkoxy compound 5 by reaction with NaH and $R^7X$ where $R^7$ and X are defined above. Catalytic hydrogenolysis over palladium on carbon of 5 affords the intermediate phenol 6. Reaction of 6 with NaH and a compound of formula $Ar^1$-$L^2$-X, where $L^2$, and X are defined above, provides 7, which is a representative compound of the invention.

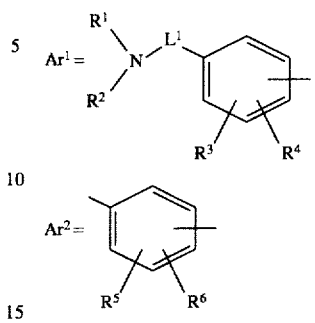

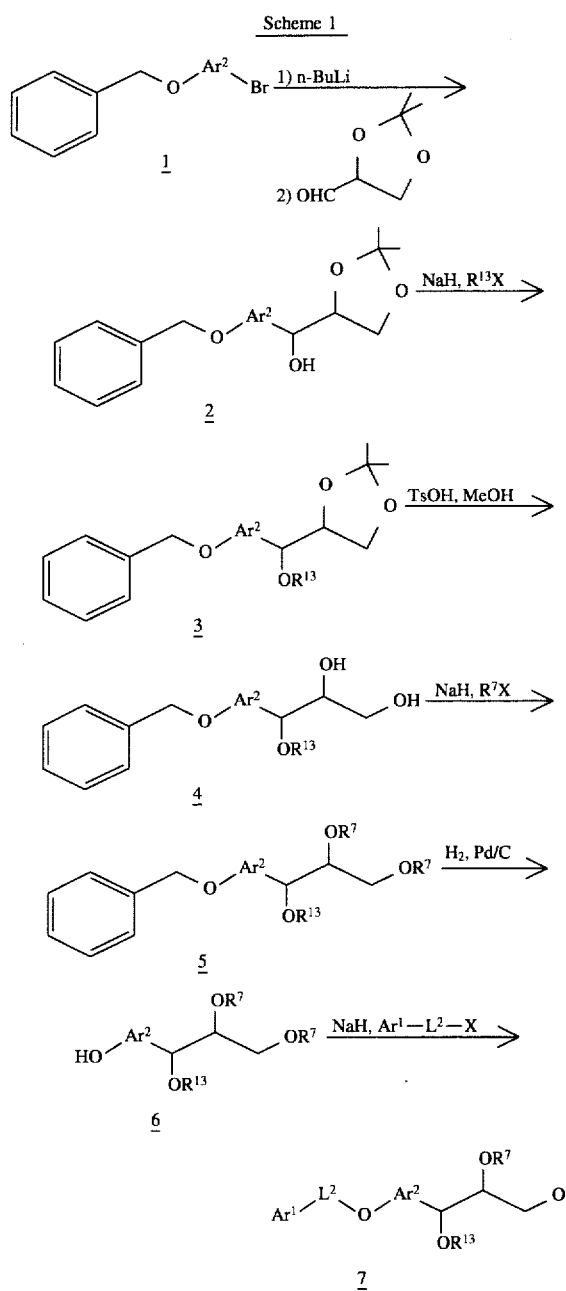

The preparation of dioxolane-containing compounds of the invention is shown in Scheme 2. Diol 4, prepared as shown in Scheme 1, is condensed with carbonyl compound $R^{15}R^{16}CO$ where $R^{15}$ and $R^{16}$ are defined above under standard ketalization conditions to provide 8. The desired compound 9.9 is then prepared by hydrogenolysis of 8, followed by alkylation of the resulting phenol with $Ar^1$-$L^2$-X as described in Scheme 1.

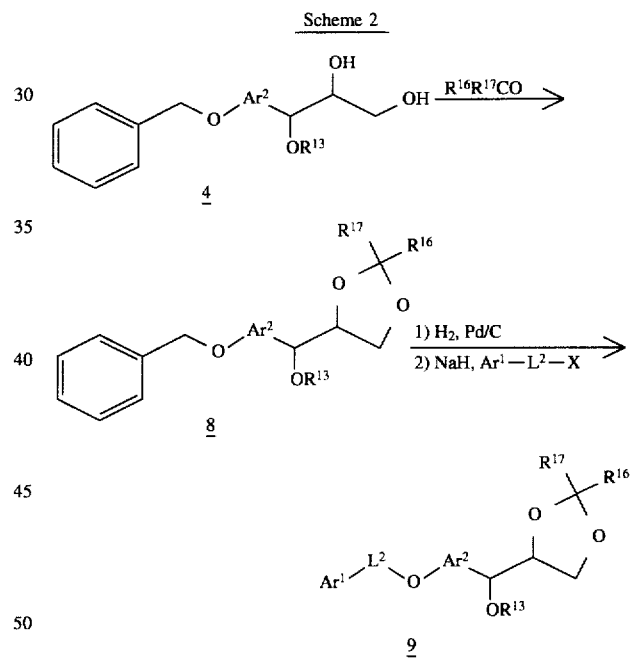

The preparation of oxime-containing compounds of the invention is shown in Scheme 3. Alcohol 2, prepared as in Scheme 1, is oxidized to ketone 10, for example using Swern oxidation conditions (Swern, D., Manusco, A. J., and Huang, S. L., *J. Org. Chem.*, 1978, 43, 2480). Reaction of 10 with $HNOR^{14}$, where $R^{14}$ is defined above affords oxime 11. Hydrolysis 11 as described in Scheme 1 provides key intermediate 12, which is converted to the desired trialkoxypropane 16 or dioxolane 15 as outlined in Schemes 1 and 2 respectively.

Scheme 3

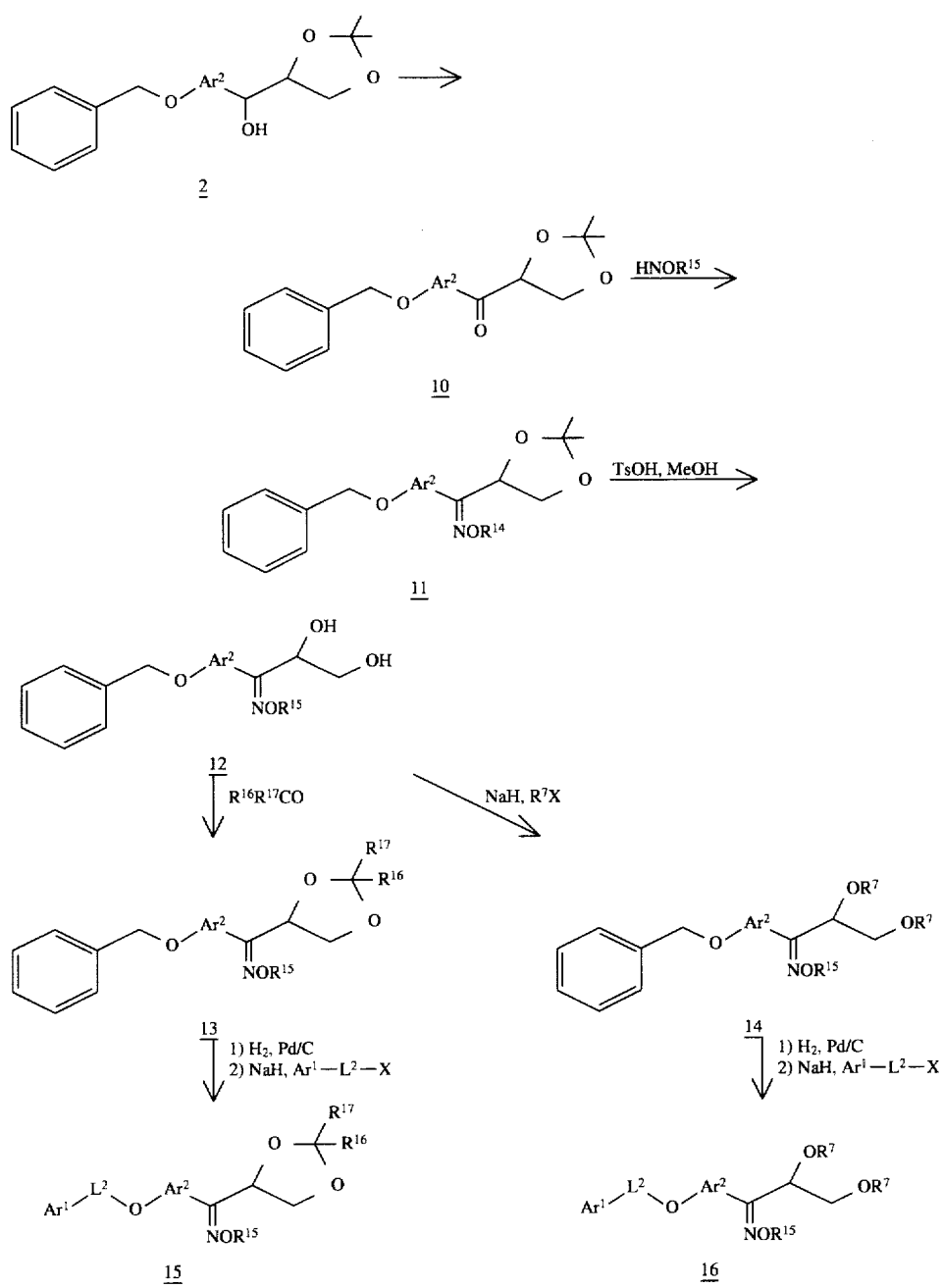

The preparation of the preferred compounds of the invention is outlined in Scheme 4. 3-(p-nitrobenzenethioxy)bromobenzene 17 was prepared by coupling of m-bromobenzenethiol and p-nitrobromobenzene. Reduction of 17, for example with potassium borohydride and CuCl, gives amine 18 which is formylated according to the procedure of Krishnamurthy (Tetrahedron Lett. 1982, 23, 3315) to provide N-formyl compound 19. Treatment of 19 with NaH and $R^1X$ where $R^1$ is alkyl and X is Br, Cl, or I, followed by hydrolysis with aqueous NaOH provides alkylamine 20. Reaction of 20 with NaH and allyl bromide provides 21, which is converted to the desired compound 22 as outlined in Schemes 1–3. Compounds in which $R^2$ is $R^9R^{10}NCO$ are prepared by treatment of 23 with a suitable base such as lithium hexamethyldisylazide and carbamoyl chloride $R^9R^{10}NCOCl$.

Scheme 4

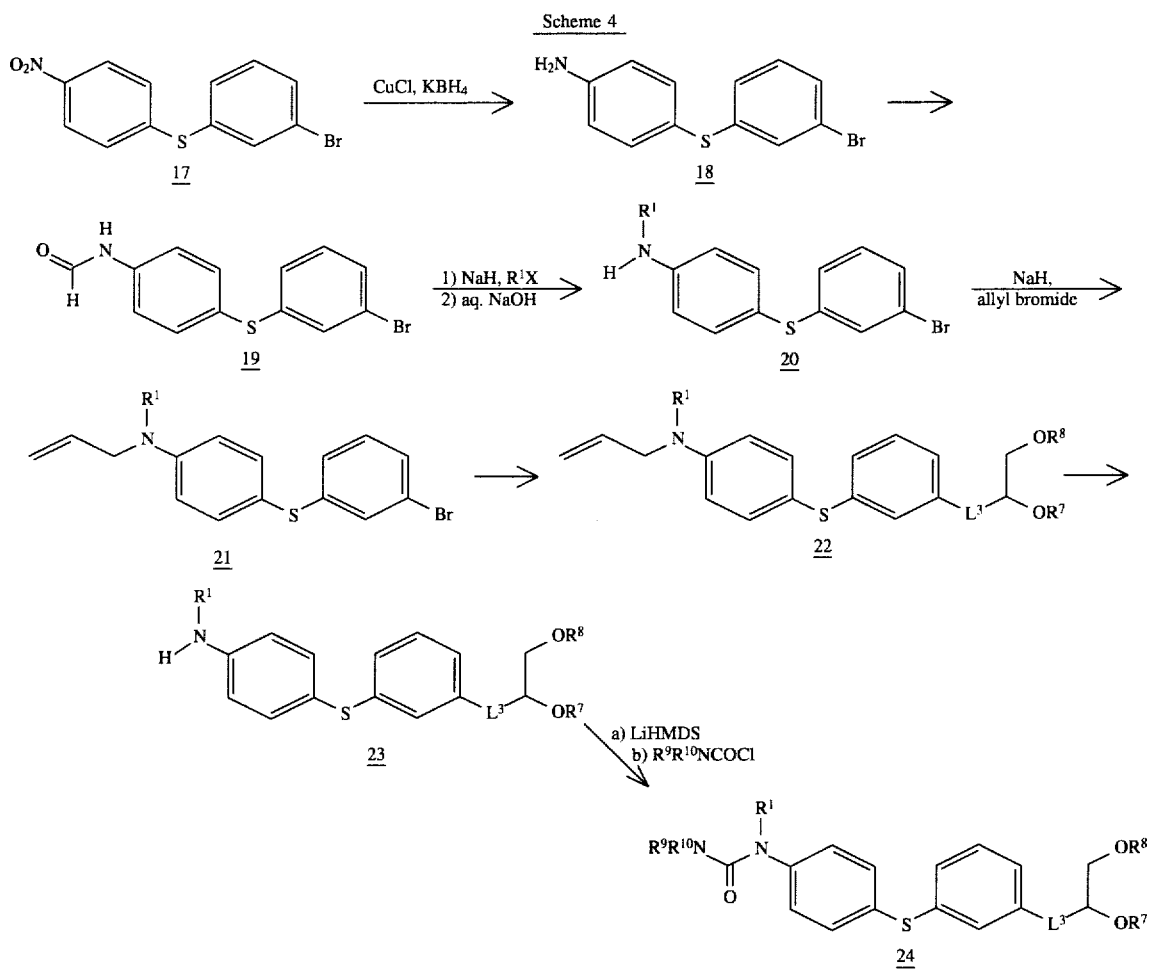

The preparation of the compounds of this invention where $R^{10}$ is haloalkyl or aminoalkyl is shown in Scheme 5. Amine 23, prepared as in Scheme 4, is treated with the desired haloalkylisocyanate to form haloalkyl derivative 25. Conversion of 25 to azide 26, for example with sodium azide, and alkylation with sodium hydride and $R^9X$ as described above provides 27, which is reduced to the desired aminoalkyl compound 28 by treatment with 1,3-propanedithiol.

Scheme 5

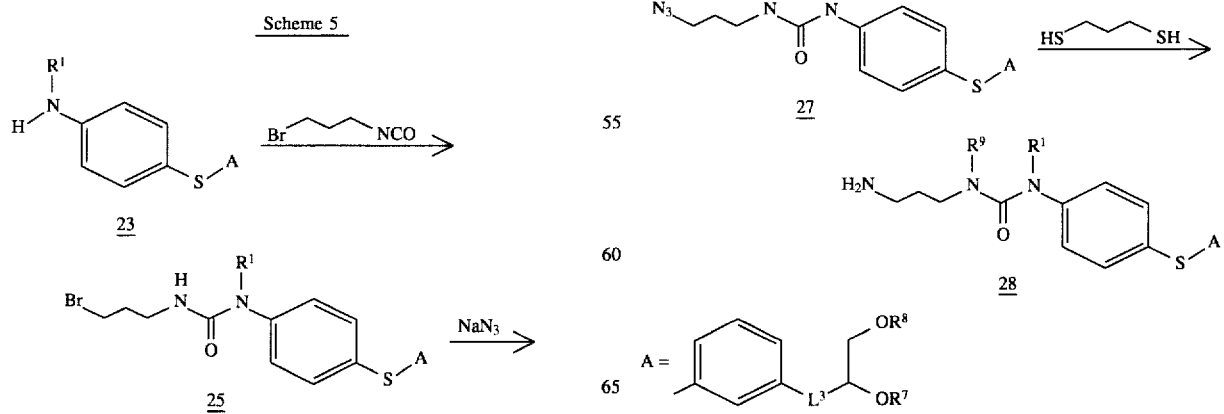

The preparation of the compounds of this invention where $R^{10}$ is hydroxyalkyl, carboxyalkyl, (alkoxycarbonyl)alkyl, or (alkylaminocarbonyl)alkyl, is shown in Scheme 6. Amine 23, prepared as in Scheme 4, is treated with an alkoxycarbonylalkylisocyanate to provide the alkoxycarbonylalkyl derivative 29, which is alkylated by treatment with NaH and R9X as described above to form 30. Hydrolysis of ester 30 provides carboxyalkyl derivative 31. Reduction of 30 with lithium borohydride or 31 with $BH_3$ provides hydroxyalkyl compound 32. The (alkylaminocarbonyl)alkyl derivatives 33 are prepared from ester 30, or acid 31 by standard synthetic methods.

Scheme 7

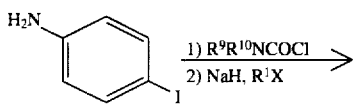

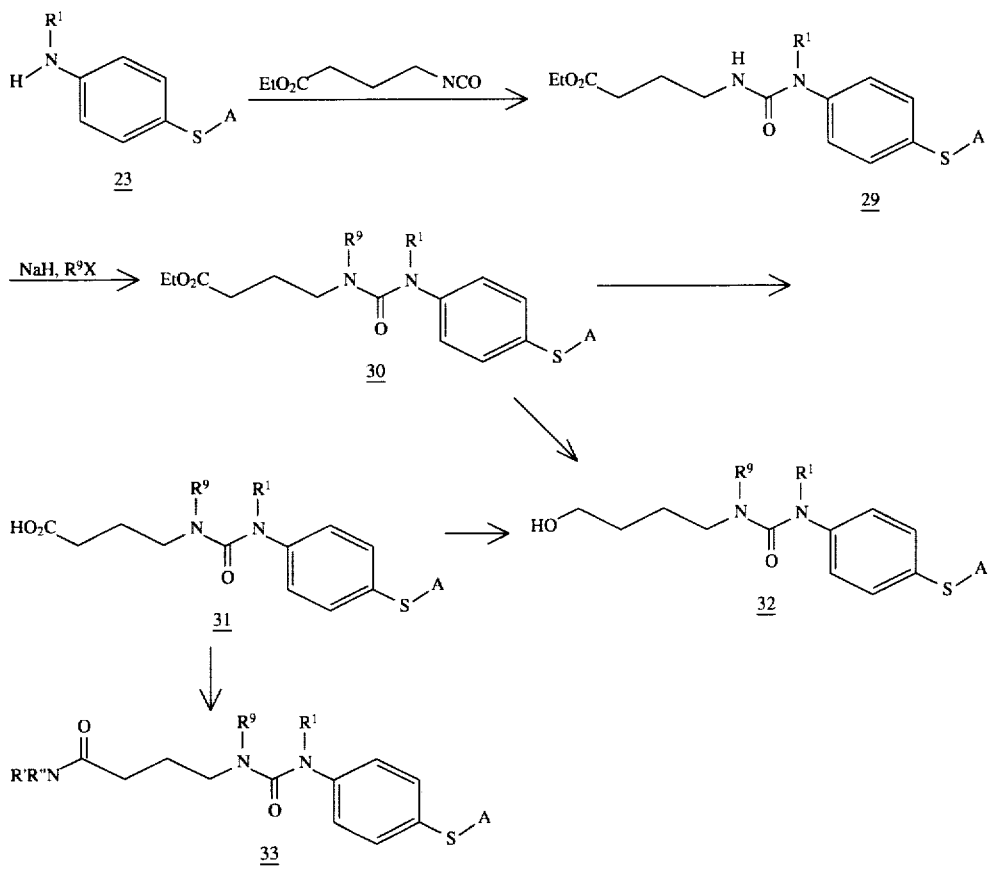

The preparation of the arylpropynyl-, arylpropenyl-, and arylpropyl-aryl ether compounds of the invention is shown in Scheme 6. 4-iodoaniline is converted to urea 34 by acylation with dimethylcarbamyl chloride, followed by alkylation with NaH and $R^1X$. Coupling of 34 with propargyl alcohol provides propynol 35 which is converted to chloride 36 by treatment with phosphorus trichloride. The desired arylpropynyl-aryl ether 37 is then prepared as described in Schemes 1–3.

Reduction of alkynol 35 with Red-Al (sodium bis(2-methoxyethoxy)aluminum hydride) provides trans allylic alcohol 38, which is converted to the desired compound 39 as described above. Catalytic hydrogenation of 39, for example with palladium on carbon, provides saturated compound 40.

-continued
Scheme 7

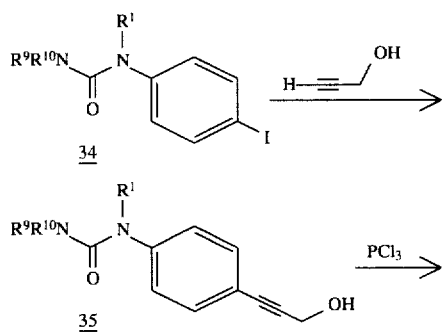

-continued
Scheme 7

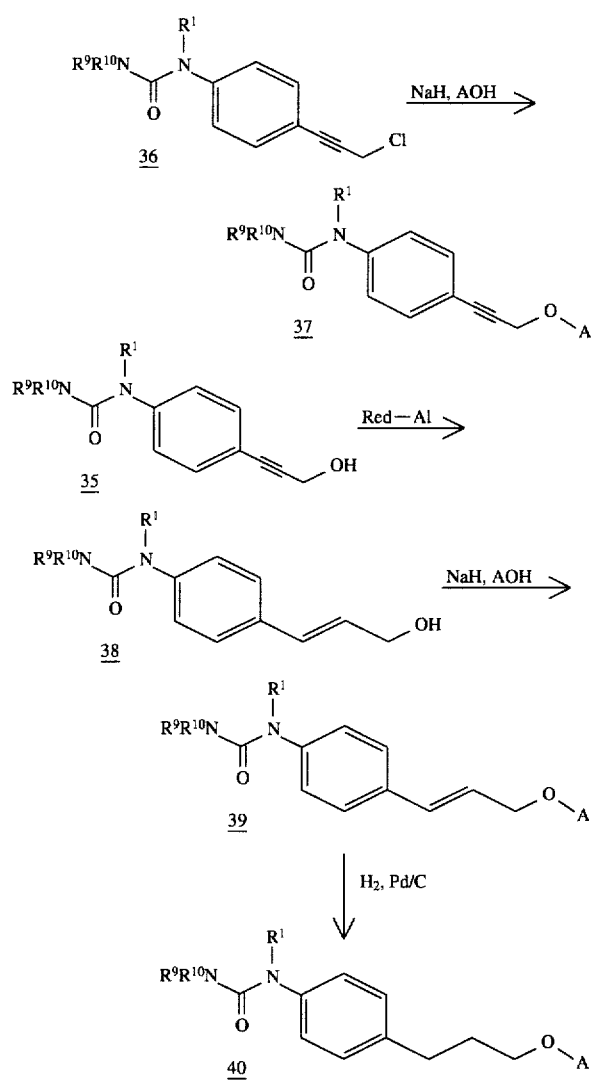

The foregoing may be better understood by the following Examples, which are presented for purposes of illustration and are not intended to limit the scope of the invention.

EXAMPLE 1

Preparation of E-(4S)-O-methyl-2,2-dimethyl-4-[(5-fluoro-3 -(4-(N',N'-dimethylaminocarbonyl-N-methylamino)benzyloxy)phenyl)oximinomethyl] -1,3-dioxolane.

Step 1: (4R, 1'R)- and(4R, 1'S)-2,2-dimethyl-4 -[(5-fluoro-3-(napth-2-ylmethoxy)phenyl)hydroxymethyl]- 1,3-dioxolane.

A flame-dried flask was charged with 3-(napth-2-ylmethoxy)-5-fluorobromobenzene (0.86 g, 2.6 mmol), prepared according to the method of EPA 385 679, a stir bar, and freshly dried tetrahydrofuran (THF, 23 mL). The resulting solution was cooled to −78 ° C. under a nitrogen atmosphere and n-butyllithium (2.5M in hexanes, 1.04 mL, 2.6 mmol) was added slowly in a dropwise fashion via syringe. After stirring for 10 minutes at −78 ° C. a THF solution (6 mL) of (R)-(+)- 2,2-dimethyl-1,3-dioxolane-4-carboxaldehyde (0.34 g, 2.6 mmol), prepared as described in Jackson, *Synthetic Commun.* 1988, 18(4), 337–341) was added. The resulting solution was stirred for 30 minutes at −78 ° C., and the cooling bath was removed. The reaction was stirred for 1 hour and then quenched with excess saturated aqueous $NH_4Cl$. The mixture was partitioned between saturated aqueous $NH_4Cl$ and ethyl acetate. The organic layer was washed twice with brine, dried over $MgSO_4$, filtered, and concentrated in vacuo to provide a cloudy oil which was purified by chromatography on silica gel (20% ether:hexanes) to give the less polar anti-(4R, 1'S) alcohol (0.193 g, 20%), a mixture of both isomers (0.233 g, 23%), and the more polar syn-(4R, 1'R) alcohol (0.149 g, 15%).

Step 2: (4R)-2,2-dimethyl-4-[(5-fluoro-3-(napth-2yl-methoxy)phenyl)carbonyl. methyl]- 1,3-dioxolane.

Following the Swern oxidation procedure (Swern, D.; Manusco, A. J.; Huang, S. L.,*J. Org. Chem.* 1978, 43, 2480) a mixture of (4R, 1'R)- and (4R, 1'S)-2,2-dimethyl-4-2,2-dimethyl-[(5-fluoro-3-(napth-2ylmethoxy)phenyl)hydroxymethyl] -1,3-dioxolane (0.55 mg, 1.44 mmol), prepared as in step 1, was oxidized to the corresponding ketone (350 mg, 66%) after chromatography on silica gel.

Step 3: Z- and E-(4S)-O-methyl-2,2-dimethyl-4-[(5-fluoro-3 -(napth-2-ylmethoxy)phenyl)oximinomethyl] -1,3-dioxolane.

To a solution of (4R)-2,2-dimethyl-4-[(5-fluoro-3-(napth-2-ylmethoxy)phenyl)carbonylmethyl] -1,3-dioxolane (50 mg, 0.132 mmol), prepared as in step 2, in ethanol (0.5 mL) were added sequentially 0-methyl-hydroxylamine hydrochloride (55 mg, 0.66 mmol) and pyridine (53 ]µL, 0.66 mmol). The resulting solution was stirred at 40° C. for 1 hour and the volatiles were removed in vacuo. The resulting residue was partitioned between ethyl acetate and water. The aqueous layer was separated and extracted twice with ethyl acetate. The combined organic layers were were washed once with saturated aqueous $NH_4Cl$, twice with brine, dried over $MgSO_4$, filtered, and concentrated in vacuo. The isomers were separated by chromatography on silica gel (1.0% ethyl acetate/hexanes) to give in the order of elution the pure Z-oxime isomer (14.5 rag, 27%), a mixture of both isomers (24.3 mg, 45%), and the pure E-oxime isomer (6.5 mg, 12%). Z-isomer: 1H NMR (300 MHz, $CDCl_3$) δ 7.83–7.90 (4H, m), 7.47–7.54 (3H, m), 7.06 (1H, br s), 6.93 (1H, ddd, J= 10, 1.5, 2.5 Hz), 6.73 (1H, dr, J= 10, 3, 3 Hz), 5.46 (1H, t, J= 7 Hz), 5.22 (2H, s), 4.43 (1H, dd, J= 7.5, 9 Hz), 3.98 (3H, s), 3.83 (1H, dd, J= 9, 7.5 Hz), 1.37 (3H, s), 1.28 (3H, s). MS m/e 410 $(M+H)^+$, 427 $(M+NH_4)^+$. Analysis calc'd for $C_{24}H_{24}NO_4F$: C, 70.40; H, 5.91; N, 3.42. Found: C, 70.30; H, 5.95; as N, 3.43. E-isomer: 1H NMR (300 MHz, $CDCl_3$) δ 7.83-7.90 (4H, m), 7.47-7.54 (3H, m), 6.84 (1H, br s), 6.70–6.78 (2H, m), 5.22 (2H, s), 4.85 (1H, t; J= 7.5 Hz), 4.12 (1H, dd, J= 7.5, 9 Hz), 3.91 (1H, dd, J= 9, 7.5 Hz), 3.84 (3H, s), 1.38 (3H, s), 1.29 (3H, s). MS m/e 410 $(M+H)^+$, 427 $(M+NH_4)^+$. Analysis calc'd for $C_{24}H_{24}NO_4F$: C, 70.40; H, 5.91; N, 3.42. Found: C, 70.30; H, 5.95; N, 3.43.

Step 4: E-(4S)-O-methyl-2,2-dimethyl-4-[(5-fluoro-3-hydroxyphen-1-yl)oximinomethyl] -1,3-dioxolane.

A flask was charged with 10% Pd/C (130 mg) and a solution in ethanol (4.5 mL) of E-(4S)-O-methyl-2,2-dimethyl-4-[(5-fluoro-3-(napth-2-ylmethoxy)phenyl)oximinomethyl] -1,3-dioxolane (450 mg, 1.1 mmol), prepared as in step 3, was added. The reaction mixture was evacuated and flushed with hydrogen (3 cycles) and maintained under 1 atmosphere of hydrogen at ambient temperature for 1 hour. The reaction mixture was flushed with nitrogen and filtered through a pad of celite. The filter cake was rinsed thoroughly with ethanol and the combined flitrates were concentrated in vacuo. Purification by chromatography on silica gel (10% ethyl acetate/hexanes) gave E-(4S)-O-methyl-2,2-dimethyl-4-[(5-fluoro-3-hydroxyphen-1-yl)oximinomethyl] -1,3-dioxolane as a colorless oil (259 mg, 86%).

Step 5: methyl 4-(N-methylaminocarbonyl)aminobenzoate.

A solution of methyl 4-aminobenzoate (15 g, 99 mmol), and methyl isocyanate (11.8 mL, 200 mmol) in toluene (400 mL) was heated at 100° C. under N2 for 3 hours during which time a precipitate formed slowly. Additional methyl isocyanate (11.8 mL, 200 mmol) was added and heating was continued for 2 hours. The reaction mixture was cooled to 0° C. and filtered. The precipitate was washed with ether and vacuum-dried to give methyl 4-(N-methylaminocarbonyl)aminobenzoate as a colorless solid (17.5 g, 85%).

Step 6: methyl 4-(N', N'-dimethylaminocarbonyl-N-methylamino)benzoate.

To a 0° C. suspension of NaH (80% oil dispersion, 3.60 g, 120 mmol) in THF (200 mL) under $N_2$ was added a solution of methyl 4-(N-methylaminocarbonyl)aminobenzoate (10.0 g, 48 mmol), prepared as in step 5, in THF (40 mL). The reaction mixture was stirred at 0° C. until gas evolution ceased, then the cold bath was removed and stirring was continued for 1.5 hours. A solution of iodomethane (6.6 mL, 106 mmol) in DMF (24 mL) was added and the reaction mixture was stirred for 72 hours at ambient temperature. NaH (2.0 g), and as iodomethane (5.0 mL) were then added and the reaction mixture was stirred for an additional 2 hours. The reaction mixture was poured slowly into ice-water and the organics were stripped off in vacuo. The aqueous solution was extracted with ethyl acetate (10 x). The combined organic layers were dried over $MgSO_4$, filtered, and concentrated. Pure methyl 4-(N', N'-dimethylaminocarbonyl-N-methylamino)benzoate (6.62 g, 58%) was obtained as a colorless oil which crystallized on standing after chromatography on silica gel (40%, then 50% ethyl acetate / hexanes). mp 71°–73° C.

Step 7: 4-(N', N'-dimethylaminocarbonyl-N-methylamino)benzyl alcohol.

To a 0° C. solution of methyl 4-(N', N'-dimethylaminocarbonyl-N-methylamino)benzoate (1.50 g, 6.35 mmol), prepared as in step 6, in THF (11.4 mL) was added lithium triethylborohydride (1.0 M solution in THF, 14 mmol). The reaction mixture was stirred for 1 hour. Water (3.0 mL) and $H_2O_2$ (30% aqueous solution, 5.0 mL) were added cautiously and the reaction mixture was stirred at 45° C. for 20 min. Aqueous HCL (6 M, 8.0 mL) was added and the reaction mixture was stirred at reflux for 14 hours. The reaction mixture was cooled to ambient temperature and poured into ethyl acetate. The aqueous phase was extracted three times with ethyl acetate. The combined organic layers were dried over $MgSO_4$, filtered, and concentrated in vacuo. 4-(N', N'-dimethylaminocarbonyl-N-methylamino)benzyl alcohol (797 mg, 61%) was isolated as a colorless solid by chromatography on silica gel (ethyl acetate). mp 65°–66° C.

Step 8: 4-(N',N'-dimethylaminocarbonyl-N-methylamino)benzyl chloride.

To a stirred solution at −23° C. under $N_2$ of 4 -(N',N'-dimethylaminocarbonyl-N-methylamino)benzyl alcohol (77.0 rag, 0.37 mmol), prepared as in step 7, in dry $CH_2Cl2$ (3.7 mL) was added triethylamine (67.0 μL, 0.48 mmol), and methanesulfonyl chloride (34.0μL, 0.44 mmol). The reaction mixture was stirred at ambient temperature until TLC indicated complete reaction (~5 hours). The resultant solution was poured into ethyl acetate and the organic phase was washed (2 X, water; 2 X, brine), dried ($MgSO_4$), filtered and concentrated in vacuo. Purification by flash chromatography on silica gel (70% ethyl acetate / hexane) provided 4 -(N',N'-dimethylaminocarbonyl-N-methylamino)benzyl chloride (56.0 mg, 67.0%) as a colorless oil which crystallized on standing at −25 ° C. mp 38.5°–39 ° C. 1H NMR (300 MHz, $CDCl_3$) δ 7.34 (2H, d, J= 8.5 Hz), 7.04 (2H, d, J= 8.5 Hz), 4.57 (2H, s), 3.22 (3H, s), 2.71 (6H, s). MS m/e 227 $(M+H)^+$, 244 $(M+NH_4)^+$. Step 9: E-(4S)-O-Methyl-2,2-dimethyl-4-[(5-fluoro-3 -(4-(N', N'-dimethylaminocarbonyl-N-methylamino)benzyloxy)phenyl)oximinomethyl- 1,3: dioxolane.

To a flask containing E-(4S)-O-methyl-2,2-dimethyl-4-[(5-fluoro-3-hydroxyphen- 1-yl)oximinomethyl]-1.3-dioxolane (160 mg, 0.59 mmol) in dry DMF (10 mL) was added sodium hydride (80% oil dispersion, 20 mg, 0.65 mmol). After gas evolution ceased, 4-(N',N'-dimethylaminocarbonyl-N-methylamino)benzyl chloride (134 mg, 0.59 mmol) was added in a single portion. The reaction was stirred for 3 hours and partitioned between ethyl acetate and saturated aqueous ammonium chloride. The aqueous layer was drawn off and extracted with ethyl acetate (3x, 10 mL). The combined organic layers were washed with brine, dried over $MgSO_4$, filtered, and concentrated in vacuo to give an orange oil. Purification by chromatography on silica gel (30% ethyl acetate:hexanes) provided pure E-(4S)-O-methyl- 2,2-dimethyl-4-[(5-fluoro-3-(4-(N', N'-dimethylaminocarbonyl-N-methylamino)benzyloxy)phenyl)oximino -1.3-dioxolane (170 mg, 62%). 1H NMR (300 MHz, CDCl3) δ7.37 (2H, d, J= 9 Hz), 7.39 (2H, d, J= 9 Hz), 6.81 (1H, br s), 6.67–6.77 (2H, m), 4.98 (2H, s), 4.86 (1H, t, J= 7.5 Hz), 4.13 (1H dd, J= 8.5, 7.5 Hz), 3.92 (1H, dd, J= 8.5, 7.5 Hz), 3.87 (3H, s), 3.23 (3H, s), 2.71 (6H, s), 1.39 (3H, s), 1.32 (3H, s). MS m/e 460 $(M+H)^+$, 477 $(M+NH_4)$. Analysis calc'd for $C_{24}H_{30}N_3O_5F$: C, 62.73; H, 6.58; N, 9.14. Found: C, 62.56; H, 6.66; N, 9.08.

EXAMPLE 2

Preparation of E-(4S)-O-methyl-2,2-dimethyl-4-[ (5-fluoro- 3-(4-(N-acetyl-N-methylamino)benzyloxy)phenyl)oximinomethyl]-1,3-dioxolane.

Step 1: 4,-(N-acetyl-N-methylamino)benzoic acid.

To a solution of N-methyl-4-aminobenzoic acid (2.0 g, 13.2 mmol) dissolved in anhydrous pyridine (13.2 mL) was added acetic anhydride (1.4 mL, 14.5 mmol). The reaction was stirred at ambient temperature until TLC indicated complete reaction (~ 22 hours). The resulting solution was poured into ethyl acetate and the organic phase was washed (3 X, 10% HCl; 1 X, water; 1 X, brine), dried ($MgSO_4$), filtered, and concentrated in vacuo to provide the corresponding amide as a colorless solid. Recrystallization (ethyl acetate / hexane) afforded pure 4-(N-acetyl-N-methylamino)benzoic acid (2.15 g, 84.0%). $^1H$ NMR (300 MHz, $CDCl_3$) δ8.18 (2H, br d, J= 8.5 Hz), 7.33 (2H, br d, J= 8.5 Hz), 3.33 (3H, s), 2.0 (3H, br s) MS m/e 194 $(M+H)^+$, 211 $(M+NH_4)^+$.

Step 2. Preparation of 4-(N-acetyl-N-methylamino)benzyl alcohol.

An oven dried flask, under nitrogen flow, was charged with a stir bar, 4-(N-acetyl-N-methylamino)benzoic acid (1.0 g, 5.18 mmol), prepared as in step 1, anhydrous DME (10.3 mL), and anhydrous DMF (3.0 mL). The resulting solution was cooled to −20 ° C., and 4-methylmorpholine (0.60 mL, 5.4 mmol) and isobutyl chloroformate (0.70 mL, 5.4 mmol) were added sequentially via syringes. The reaction mixture was stirred under $N_2$ at −20° C. for 1 h. The resulting yellow mixture was filtered and the precipitate washed with DME (2 X, ~1 mL). The combined filtrate and washings were cooled to 0° C. and a solution of sodium borohydride (800 mg, 21.1 mmol) in water (2.0 mL) was added dropwise. The reaction was stirred at 0° C. for 15 min. and quenched with saturated aqueous ammonium chloride. The resulting mixture was partitioned between ethyl acetate and brine. The combined organic layers were dried (MgSO$_4$), filtered and concentrated in vacuo to give an oil. Purification by flash chromatography on silica gel (90% ethyl acetate / hexane) provided the corresponding alcohol as a colorless oil which solidified on standing. Recrystallization from hexane provided 4-(N-acetyl-N-methylamino)benzyl alcohol as a colorless solid (543.0 mg, 58.5%). $^1$H NMR (300 MHz, CDCl$_3$) δ7.45 (2H, d, J = 8.5 Hz), 7.18 (2H, d, J= 8.5 Hz), 4.75 (2H, s), 3.27 (3H, s), 1.90 (3H, br MS m/e 180 (M+H)$^+$, 197 (M+NH$_4$)$^+$.

Step 3. Preparation of 4-(N-acetyl-N-methylamino)benzyl bromide.

To a solution of 4-(N-acetyl-N-methylamino)benzyl alcohol (543.0 mg, 3.0 mmol), prepared as in step 2, dissolved. in dry CH$_2$Cl$_2$ (11.5 mL) was added dropwise 1M PBr$_3$ in CH$_2$Cl$_2$ (3.6 mL, 3.6 mmol) at 0° C. The reaction was stirred at ambient temperature until TLC indicated complete reaction (~ 5 hours). The resulting solution was partitioned between ethyl acetate and brine. The combined organic layers were decolorized with charcoal, dried (MgSO$_4$), filtered through celite and concentrated in vacuo. Purification by flash chromatography on silica gel (40% ethyl acetate / hexane) provided 4-(N-acetyl-N-methylamino)benzyl bromide as a colorless solid (595 mg, 81.0%). $^1$H NMR (300 MHz, CDCl$_3$) δ7.46 (2H, d, J= 8.5 Hz), 7.18 (2H, d, J= 8.5 Hz), 4.50 (2H, s), 3.27 (3H, s), 1.88 (3H, br s). MS m/e 242 (M+H)$^+$, 259/261 (M+NH$_4$)$^+$. Analysis calc'd for C$_{10}$H$_{12}$NOBr: C, 49.61; H, 5.00; N, 5.79. Found: C, 49.35; H, 4.97; N, 5.65.

Step 4: E-(4S)-O-methyl-2,2-dimethyl-4-[(5-fluoro-3 -(4-(N-acetyl-N-methylamino)benzyloxy)phenyl)oximinomethyl] -13-dioxolane.

The desired compound was prepared according to the method of Example 1, step 9, except substituting 4-(N-acetyl-N-methylamino)benzyl bromide, prepared as in step 3, for 4-(N',N'-dimethylaminocarbonyl-N-methylamino)benzyl chloride. Chromatography on silica gel (50% ethyl acetate:hexanes) provided E-(4R)-O-methyl- 2,2-dimethyl -4- [(5-fluoro-3-(4-(N-acetyl-N-methylamino)benzyloxy)phenyl )oximinomethyl]-1,3-dioxolane. $^1$H NMR (300 MHz, CDCl$_3$) δ7.48 (2H, d, J= 9 Hz), 7.22 (2H, d, J= 9 Hz), 6.82 (1H, br s), 6.76 (1H, br d, J= 9.5 Hz), 6.72 (1H, dr, J= 10.5, 3 Hz), 5.06 (2H, s), 4.87 (1H, tt, J= 7 Hz), 4.13 (1H, dd, J= 7.5, 8 Hz), 3.92 (1H, dd, J= 7.5, 9 Hz), 3.87 (3H, s), 3.28 (3H, br s), 1.89 (3H, br s), 1.39 (3H; s], 1.32 (3H, s). MS m/e 43 1 (M+H)$^+$, 448 (M+NH$_4$)$^+$. Analysis calc'd for C$_{23}$H$_{27}$N$_2$O$_5$F(0.25 H$_2$O): C, 63.51; H, 6.37; N, 6.44. Found: C, 63.39; H, 6.37; N, 6.34.

EXAMPLE 3

Preparation of Z- and E-(4S)-O-methyl-2,2 -dimethyl-4-[(3-(4-(N-allyl-N-methylamino)phenylthioxyl) -1,3-dioxolane.

Step 1:3 -(p-nitrobenzenethioxy)bromobenzene.

A 500 mL round bottomed flask equipped with a magnetic stirbar was charged with sodium hydride (3.78 g of a 60% oil dispersion, 95 mmol), and freshly dried THF (200 mL) under a stream of nitrogen. To the stirred suspension was added t-butanol (8 mL). When hydrogen gas evolution ceased, m-bromobenzenethiol (12.0 g, 63 mmol) was via syringe over 5 rain and the resulting solution was stirred for 10 min. To this solution was added in a single portion p-nitrobromobenzene (10.7 g, 52.9 mmol). The solution was stirred at room temperature for 45 min and sodium hydride (0.5 g of a 60% oil dispersion, 12.5 mmol) was added. After 30 min m-bromobenzenethiol (1.0 mL, 9.7 mmol) was added and the reaction was judged to be complete 30 min later by tlc. The reaction mixture was partitioned between saturated aqueous ammonium chloride and ethyl acetate. The layers were separated and the aqueous layer was extracted with ethyl acetate (3x, 100 mL). The combined organic extracts were washed (1x, 15% aqueous sodium hydroxide; 2x, brine), dried (Na$_2$SO$_4$), filtered and concentrated in vacuo to to ~400 mL. Decolorizing carbon was added to the organic extracts and the solution was filtered through a celite pad as and concentrated in vacuo to give the unpurified product as an orange solid (19.4 g). The solid was taken up in ether and treated with decolorizing carbon, filtered through celite, and the volatiles removed in vacuo. Two recrystallizations from ether/hexanes provided pure 3-(p-nitrobenzenethioxy)bromobenzene.

Step 2: 3-(p-aminobenzenethioxy)bromobenzene.

To a THF (15 mL) solution of 3-(p-nitrobenzenethioxy)bromobenzene (2.0 g, 6.4 mmol), prepared as in step 1, was added methanol (50 mL) and CuC$_1$ (0.89 g, 99%, 9.0 mmol). The solution was cooled to ~10° C. in an icebath and solid potassium borohydride (1.13 g, 21 mmol) was added in small portions while maintaining the reaction temperature below 20° C. After complete addition of potassium borohydride the icebath was removed. The reaction was judged to be complete after 20 min and was quenched by adding water (40mL) while maintaining the reaction temperature under 20° C. The quenched reaction mixture was filtered through celite and partitioned between ether and water. After separating the layers the aqueous layer was extracted three times with ether. The combined organic layers were washed twice with brine and concentrated to ½ the original volume. The solution was treated with decolorizing carbon while drying over MgSO$_4$, filtered through a celite pad, and concentrated in vacuo to give 3-(p-aminobenzenethioxy)bromobenzene (1.81 g, 101%) as a waxy red solid which was carried on without further purification.

Step 3: 3-(N-formyl-p-aminobenzenethioxy)bromobenzene.

3-(p-aminobenzenethioxy) bromobenzene (1.13 g, 4.1 mmol), prepared as in step 2 was formylated according to the procedure of Krishnamurthy (Tetrahedron Lett. 1982, 23, 33 15). The reaction mixture was partitioned between ether and saturated aqueous sodium bicarbonate. The layers were separated and the aqueous layer was extracted three times with ether. The combined organic layers were washed once with brine, treated with decolorizing carbon and MgSO$_4$, filtered through a celite pad, and concentrated in vacuo to give 3-(N-formyl-p-aminobenzenethioxy)bromobenzene as a light brown oil (1.31 g, 104%) which was carried on without further purification.

Step 4: 3-(N-methyl-p-aminobenzenethioxy)bromobenzene.

A flask equipped with a magnetic stirbar was charged under a stream of nitrogen with freshly dried THF (100 mL) and sodium hydride (2.75 g, 60% oil dispersion, 69 mmol). A solution in dry THF of 3-(N-formyl-p-amino-benzene thioxy)bromobenzene (17.63 g, 57.4 mmol), prepared as in step 3, was added slowly. After foaming ceased dry DMF (100 mL) and methyl iodide (5.75 mL; plug filtered through neutral alumina) were added. The reaction was stirred at ambient temperature for 1.5 hours when the reaction was judged to be complete by tlc. The reaction was quenched with excess saturated aqueous ammonium chloride and partitioned between water and ether. The layers were separated and the aqueous layer was extracted with three times with ether. The combined organic layers were washed twice with brine, dried over MgSO$_4$, filtered, and concentrated in vacuo to give the alkylated compound (24.74 g). The resulting residue was dissolved in ethanol (230 mL), 15% aqueous sodium hydroxide was added, and the resulting mixture was heated at 60° C. for 0.5 hours and at 80° C. for 0.5 hours. The reaction mixture was cooled in an icebath and neutralized to pH~7 with 10% aqueous HCl. The resulting mixture was partitioned between ether and water. The layers were separated and the aqueous layer was extracted with three times with ether. The combined organic layers were washed twice with saturated aqueous NH$_4$C$_1$, twice with brine, dried over MgSO$_4$, filtered, and concentrated in vacuo to give 15.95 g of crude product. Purification by chromatography on silica gel (5% ethyl acetate:hexanes) provided pure 3-(N-methyl-p-aminobenzenethioxy)bromobenzene (12.21 g, 73%).

Step 5: 3-(N-allyl-N-methyl-p-aminobenzenethioxy)bromobenzene.

A flask was charged with potassium hydride (0.3 g, 35% oil dispersion, 2.62 mmol) and dry THF (1.5 mL) under a stream of nitrogen. A solution of 3-(N-methyl-p-aminobenzenethioxy)bromobenzene (0.50 g, 1.71 mmol), prepared as in step 4, in dry THF was added via syringe. When gas evolution ceased, allyl bromide (0.38 mL, 4.27 mmol, passed through a neutral alumina pad before addition) was added in a single portion, followed by dry DMF (3.4 mL). After 15 min the reaction was quenched with isopropanol and partitioned between saturated aqueous NH$_4$C$_1$ and ethyl acetate. The layers were separated and the aqueous layer was extracted with ethyl acetate. The combined organic layers were washed twice with brine, dried over MgSO$_4$, filtered, and concentrated in vacuo to give 0.91 g of crude product. Purification by chromatography on silica gel (5% ethyl acetate:hexanes) provided pure 3-(N-allyl-N-methyl-p-aminobenzenethioxy)bromobenzene (0.43 g, 75%).

Step 6: (4R, 1'R) and (4R, 1'S)-2,2-dimethyl-4-[(3 -(4-(N-allyl-N-methylamino)phenylthioxyl)phenyl)hydroxymethyl]- 1,3-dioxolane.

The desired compound was prepared according to the method of Example 1, step 1, except substituting 3-(N-allyl-N-methyl-p-aminobenzenethioxy)bromobenzene for 3-(napth-2-ylmethoxy)-5-fluoro-bromobenzene. The mixture of alcohols was not separated during purification.

Step 7:E- and Z-(4S)-O-methyl-2,2-dimethyl-4-[(3-(4-(N-allyl-N-methylamino) phenylthioxyl)phenyl)oximinomethyl]-1,3-dioxolane.

The desired compounds were prepared according to the method of Example 1, steps 2 and 3, except substituting 124R, 1'R) and (4R, 1'S)-4-[(3-(4-(N-allyl-N-methyl phenylthioxyl)phenyl)hydroxymethyl]-1,3-dioxolane (2.02 g, 5.25 mmol), prepared as in step 6, for (4R, 1'R)- and (4R, 1'S)-2,2-dimethyl-4 -[(5-fluoro- 3-(napth-2-ylmethoxy)phenyl)hydroxymethyl]-1,3-dioxolane. The oxime isomers (871 mg, 46%) were isolated by chromatography on silica gel (7% ethyl acetate:hexanes). Z-(4S)-O-Methyl-2,2-dimethyl-4-[(3-(4-(N-allyl-N-methylamino) phenylthioxyl)phenyl)oximinomethyl]-1,3-dioxolane, which solidified on standing, was recrystallized from cold ether/ethyl acetate mp 49°-50° C. $^1$H NMR (300 MHz, CDCl$_3$) δ7.25–7.43 (4H, m), 7.28 (1H, t, J= 8 Hz), 7.08 (1H, br d, J= 8 Hz 6.72 (2H, br d, J= 6 Hz), 5.84 (1H, octet, J= 5.5, 14, 17 Hz), 5.42 (1H, t, J= 7.5 Hz), 5.18 (1H, br d, J= 14 Hz), 5.16 (1H, br d, J= 17 Hz), 4.42 (1H, t, J= 7.5 Hz), 3.93–3.96 (5H, m), 3.81 (1H, t, J= 7.5 Hz), 2.98 (3H, s), 1.34 (3H, s), 1.23 (3H, s). MS m/e 413 (M+H)$^+$. Analysis calc'd for C$_{23}$H$_{28}$N$_2$O$_3$S: C, 66.96; H, 6.84; N, 6.79. Found: C, 66.91; H, 6.93; N, 6.79. E-(4S)-O-methyl-2,2-dimethyl- 4-[(3-(4-(N-allyl-N-methylamino) phenylthioxyl)phenyl)oximinomethyl]-1,3dioxolane was an oil. $^1$H NMR (300 MHz, CDCl$_3$) δ7.36 (2H, d, J= 8.5 Hz), 7.22 (1H, d, J= 7.5 Hz), 7.17 (1H, br s), 7.09 (1H, br t, J= 6.5 Hz), 6.75 (2H, br s) 5.87 (1H, octet, J= 5.5, 10, 18 Hz), 5.19 (1H, br d, J= 10 Hz), 5.17 (1H, br d, J = 18 Hz), 4.82 (1H, t, J= 7 Hz), 4.18 (1H, dd, J= 7, 8.5 Hz), 3.95 (2H, dr, J= 5.5, 1,1 Hz), 3.83–3.85 (4H, m), 2.98 (3H, s), 1.37 (3H, s), 1.26 (3H, s). MS m/e 413 (M+H)$^+$. Analysis calc'd for C$_{23}$H$_{28}$N$_2$O$_3$S: C, 66.96; H, 6.84; N, 6.79. Found: C, 66.98; H, 6.82; N, 6.71.

EXAMPLE 4

Preparation of Z-(4S)-O-methyl-2,2-dimethyl-4-[(3 -(4-(N',N'-dimethylaminocarbonyl-N-methylamino)phenylthioxyl)phenyl)oximinomethyl] -1,3-dioxolane.

Step 1:Z-(4R)-O-methyl-2,2-dimethyl-4-[(3-(4-N-methylaminophenylthioxy)phenyl)oximinomethyl] -1,3-dioxolane.

To an ethanol (22 mL) solution of Z-(4S)-O-methyl-2,2 -dimethyl-4-[(3-(4-(N-allyl-N-methylamino)phenylthioxyl)phenyl)oximinomethyl] -1,3-dioxolane (268 mg, 0.65 mmol), prepared as in Example 3, was added tris(triphenylphosphine)ruthenium(II) chloride (120 mg, 0.13 mmol). The resulting solution was heated at 80° C. for 30 min, another portion of the ruthenium catalyst (120 mg, 0.13 mmol) was added, and the reaction was stirred until it cooled to ambient temperature. The volatiles were removed in vacuo and the residue was partitioned between water and ethyl acetate. After separating the layers the aqueous layer was extracted with ethyl acetate. The combined organic layers were washed with brine, dried over MgSO$_4$, filtered and concentrated in vacuo. The resulting oil was purified by chromatography on silica gel (30% ethyl actetate:hexanes) to provide Z-(4S )-O-methyl-2,2-dimethyl-4- [ (3-(4- N-methylaminophenylthioxyl)phenyl)oximinomethyl] -1,3-dioxolane (227 mg, 94%). Step 2: Z-(4S)-O-Methyl-2,2-dimethyl-4-[(3 -(4-(N',N'-dimethylaminocarbonyl-N-methylamino)phenylthioxyl)phenylthioxyl)phenyl) oximinomethyl] -1,3-dioxolane.

To a solution of Z-(4S)-O-methyl-2,2-dimethyl-4-[(3-(4-N-methylaminophenylthioxyl)phenyl)oximinomethyl] -1,3-dioxolane (100 mg, 0.27 mmol), prepared as in step 1, in dry THF at −78° C. was added lithium hexamethyldisilazide (LiHMDS, 403 μL, 1M solution in THF, 0.40 mmol ). After stirring in the cold for 10 min dimethylcarbamoyl chloride (37μL, 0.40 mmol) was added via syringe in a single portion. The cooling bath was removed and the reaction mixture was stirred for 30 min at ambient temperature. The reaction was quenched by adding excess water and partitioning the resulting mixture between saturated aqueous NH$_4$Cl and ethyl acetate. After separating the layers, the aqueous layer was extracted 3 times with ethyl acetate. The combined organic layers were washed with brine, dried over MgSO$_4$, filtered and concentrated in vacuo. The resulting oil was purified by chromatography on silica gel (50% ethyl actetate:hexanes) to provide Z-(4S)-O-methyl- 4-[(3-{4-(N',N'-dimethylaminocarbonyl-N-methylamino)phenylthioxyl)phenyl)oximinomethyl] -1,3-dioxolane as an oil which crystallized upon dissolving in ethyl acetate and cooling (58 mg, 44%). mp 102°–103 ° C. $^1$H NMR (300 MHz, CDCl$_3$) δ7.52 (1H, m), 7.37–7.43 (1H, m), 7.26–7.33 (4H, m), 6.98 (2H, d, J= 8 Hz), 5.44 (1H, t, J= 7.5 Hz), 4.44 (1H, dd, J=7.5, 8.5 Hz), 3.95 (3H, s), 3.82 (1H, dd, J= 7.5, 8.5 Hz), 3.21 (3H, s), 2.72 (6H, s 1.34 (3H, s), 1.23 (3H, s). MS m/e 444 (M+H)+, 461 (M+NH$_4$)+. Analysis calc'd for C$_{23}$H$_{29}$N$_3$O$_4$S: C, 62.28; H, 6.59; N, 9.47. Found: C, 62.18; H, 6.71; N, 9.23.

EXAMPLE 5

Preparation of
E-(4S)-O-methyl-2,2-dimethyl-4-[(3-(4-(N',N': dimethylaminocarbonyl-N-methylamino) phenylthioxyl)phenyl)oximinomethyl]-1,3: dioxolane.

The desired compound was prepared as described in Example 4 except substituting E-(4S)-O-methyl-2,2-dimethyl-4-[(3-(4-(N-allyl-N-methylamino)phenylthioxyl)phenyl)oximinomethyl] -1,3-dioxolane (290 mg, 0.70 mmol) for Z-(4S)-O-methyl-2,2-dimethyl-4-[(3-(4-(N-allyl-N-methylamino)phenylthioxyl)phenyl)oximinomethyl -1,3-dioxolane. Purification by chromatography on silica gel (50% ethyl acetate:hexanes) provided E-(4S)-O-methyl 2,2-dimethyl-4- [ (3-(4-(N', N'-dimethylaminocarbonyl-No methylamino)phenylthioxyl)phenyl)oximinomethyl]-1,3-dioxolane (121 rag, 58%) as an oil. 1H NMR (300 MHz, CDCl$_3$) t) 7.22–7.38 (6H, m), 6.98 (2H, d, J= 8 Hz), 4.84 (1H, t, J= 7.5 Hz), 4.13 (1H, dd, J= 7.5, 8.5 Hz), 3.87 (1H, dd, J= 7.5, 8. Hz), 3.84 (3H, s), 3.22 (3H, s), 2.72 (6H, s), 1.38 (3H, s), 1.25 (3H, s). MS m/e 444 (M+H)+, 46 1 (M+NH$_4$)+. Analysis calc'd for C$_{23}$H$_{29}$N$_3$O$_4$S: C, 62.28; H, 6.59; N, 9.47. Found: C, 61.91; H, 6.68; N, 9.15.

EXAMPLE 6

Preparation of Z- and
E-(4R)-O-methyl-2,2-dimethyl-4-[(3-(4 -(N-allyl-N-methylamino)phenylthioxyl) oximinomethyl]-1,3-dioxolane.

Step 1: (S) -(–)2,2-dimethyl-1,3-dioxolane-4-carboxaldehyde.

The desired compound was prepared as described in Jackson, *Synthetic Commun.* 1988, 18(4), 337–341), except starting with L-(S)-glyceraldehyde, prepared as described by Hubschwerlen, C. *Synthesis,* 1986, 962–964, instead of D-(R)-glyceraldehyde.
Step2: Z-(4R)-O-methyl-2,2-dimethyl-4-[(3 -(4-(N-allyl-N-methylamino)phenylthioxyl)phenyl)oximinoethyl[- 1,3-dioxolane.
The desired compounds are prepared according to the method of Example 1, steps 1–3, except substituting (S)-(–)-2,2-dimethyl-1,3-dioxolane-4-carboxaldehyde, prepared as in step 1, for (R)-(–)-2,2-dimethyl-1,3-dioxolane-4-carboxaldehyde, and substituting 3-(N-allyl-N-methyl-p-aminobenzenethioxy)bromobenzene, prepared as in Example 3, step 5, for 3-(napth-2-ylmethoxy)-5-fluoro-bromobenzene.

EXAMPLE 7

Preparation of Z- and
E-(4R)-O-methyl-2,2-dimethyl-4-[(3-(4 -(N',N'-dimethylaminocarbonyl-N-methylamino) phenylthioxyl}phenyl)oximinomethyl]-1,3-dioxolane.

The desired compounds are prepared according to the method of Example 4, except substituting Z- and E-(4R)-O-methyl-2,2-dimethyl-4-[(3-(4-(N-allyl-N-methylamino)phenylthioxyl)phenyl)oximinomethyl] -1,3-dioxolane, prepared as in Example 6, for Z-(4S)-O-methyl-2,2-dimethyl-4-[(3-(4-(N-allyl-N-methylamino)phenylthioxyl)phenyl)oximinomethyl] -1,3-dioxolane.

EXAMPLE 8

Preparation of
E-(4R)-O-methyl-2,2-dimethyl-4-[(5-fluoro-3 -(4-(N',N'-dimethylaminocarbonyl-N-methylamino)benzyloxy)phenyl)oximinomethyl] -1,3dioxolane.

The desired compound was prepared according to the method of Example 1, except substituting (S)-(–)-2,2-dimethyl-1,3-dioxolane-4-carboxaldehyde, prepared as in Example 6, step 1, for (R)-(–)-2,2-dimethyl-1,3-dioxolane-4-carboxaldehyde. $^1$H NMR (300 MHz, CDCl$_3$) δ7.37 (2H, d, J= 9 Hz), 7.39 (2H, d, J= 9 Hz), 6.81 (1H, br s), 6.67–6.77 (2H, m), 4.98 (2H, s), 4.86 (1H, t, J= 7.5 Hz), 4.13 (2H, dd, J= 8.5, 7.5 Hz), 3.92 (1H, dd, J= 8.5, 7.5 Hz), 3.87 (3H, s), 3.23 (3H, s), 2.71 (6H, s), 1.39 (3H, s), 1.32 (3H, s). MS m/e 460 (M+H)+, 477 (M+NH$_4$). Analysis calc'd for C$_{24}$H$_{30}$N$_3$O$_5$F: C, 62.73; H, 6.58; N, 9.14. Found: C, 65.28; H, 5.83; N, 6.12 .

EXAMPLE 9

Preparation of E- and
Z-(4S)-2,2-dimethyl-4-[(3-(4-(N-allyl-N-methylamino) phenylthioxyl)phenyl)oximinomethyl]-1,3-dioxolane.

The desired compounds are prepared according to the method of Example 1, steps 2 and 3, except substituting 3-(N-allyl-N-methyl-p-aminobenzenethioxy)bromobenzene, prepared as in Example 3, step 5, for 5-fluoro-3-(napth-2-ylmethoxy)bromobenzene, and substituting hydroxylamine hydrochloride for O-methylhydroxylamine hydrochloride.

EXAMPLE 10

Preparation of Z- and
E-(4S)-O-methyl-2,2-dimethyl-4-[(3 -(4-(N-allyl-N-methylamino)phenylsulfinyl) phenyl)oximino -1,3-dioxolane.

The desired compounds are prepared by oxidation of Z- and E-(4S)-O-methyl- 4-2,2-dimethyl-[(3-(4-(N-allyl-N-methylamino)phenylthioxyl)phenyl)oximinomethyl] -1,3-dioxolane, prepared as in Example 3, with sodium metaperiodate as described in EPA 409 413 (Example 7).

EXAMPLE 11

Preparation of Z- and
E-(4S)-O-methyl-2,2-dimethyl-4-[(3 -(4-(N-allyl-N-methylamino)phenylsulfonyl)phenyl) oximinomethyl]-1,3-dioxolane.

The desired compounds are prepared by oxidation of Z- and E-(4S)-O-methyl 4-2,2-dimethyl- [ (3-(4-(N-allyl-N-methylamino)phenylthioxyl)phenyl)oximinomethyl] -1,3-dioxolane, prepared as in Example 3, with potassium peroxymonosulfate as described in EPA 409 413 (Example 14).

EXAMPLE 12

Preparation of Z- and E-(4S)-O-methyl-2,2-dimethyl-4-[(3-(4-(N',N'-dimethylaminothiocarbonyl-N-methylamino)phenylthioxyl)phenyl)oximinomethyl] 1,3-dioxolane.

The desired compound is prepared by treatment of Z- and E-(4S)-O-methyl-4- 2,2-dimethyl- [(3-(4-(N', N'-dimethylaminocarbonyl-N-methylamino)phenylthioxyl)phenyl)oximinomethyl] -1,3-dioxolane, prepared as in Examples 4 and 5, with Lawesson's Reagent ([2,4-bis-(4-methoxyphenyl)-1,3-dithia- 2,4-diphosphetane-2,4-disulfide) according to the method of Katah, A., Kashima, C., and Omote, Y., Heterocycles, 1982, 19 (12), 2283.

EXAMPLE 13

Preparation of Z- and E-(4S)-O-methyl-2,2-dimethyl-4-(5-fluoro-3 -(4-((N',N'-dimethylaminocarbonyl)-N-methylamino)benzylthioxy)phenyl)oximinomethyl] -1,3-dioxolane.

Step 1: Z- and E-(4S)-O-methyl-2,2-dimethyl-4-2,2-dimethyl-[(5 -fluoro-3-(benzylthioxy)phenyl)oximinomethyl] -1,3-dioxolane.

The desired compounds are prepared according to the method of Example 1, steps 1–3, except substituting 5-fluoro-3-benzylthiobromobenzene, prepared as described in EPA 420 511 (Example 4), for 3-(napth-2-ylmethyloxy)-5-fluorobromobenzene.

Step 2: Z- and E-(4S)-O-methyl-2,2-dimethyl-4-1(5-fluoro-3-mercaptophenyl)oximinomethyl] -1,3-dioxolane.

The desired compounds are prepared by debenzylation of Z- and E-(4S)-O-methyl- 2,2-dimethyl-4-[(5-fluoro-3-(benzylthioxy)phenyl)oximinomethyl]-1,3-dioxolane, prepared in step 1, with benzoyl peroxide as described in EPA 420 511 (Example 4).

Step 3: Z- and E-(4R)-O-methyl-2,2-dimethyl-4-(5-fluoro-3 -(4-((N',N'-dimethylaminocarbonyl)-N-methylamino)benzylthioxy)phenyl)oximinomethyl] -1,3-dioxolane.

The desired compounds are prepared according to the method of Example 1, step 9, except substituting Z- and E-(4S)-O-methyl-2,2-dimethyl-4 -[(5-fluoro-3-mercaptophenyl)oximinomethyl -1,3-dioxolane, prepared as in step 2, for E-(4S)-O-methyl- 2,2-dimethyl-[(5-fluoro-3-hydroxyphen-1-yl)oximinomethyl]-1,3-dioxolane.

EXAMPLE 14

Preparation of anti-(1S, 2R)-1 -[(5-fluoro-3-(4-(N',N'-dimethylaminocarbonyl-N-methylamino) 1-1,2,3-trimethoxypropane.

Step 1: (4R, 1'-R)- and (4R, 1'S):2,2 -dimethyl-4,2,2-dimethyl-[(5-fluoro-3-(napth-2-ylmethyloxy)phenyl]hydroxymethyl] -1,3-dioxolane.

A flame-dried flask was charged with 3-(napth-2-ylmethyloxy)-5-fluorobromobenzene (0.86 g. 2.6 mmol), prepared according to the method of EPA 385 679, a stir bar, and freshly dried tetrahydrofuran (THF, 23 mL). The resulting solution was cooled to −78° C. under a nitrogen atmosphere andn-butyllithium (2.5M in hexanes, 1.04 mL, 2.6 mmol) was added slowly in a dropwise fashion via syringe. After stirring for 10 minutes at −78° C. a THF solution (6 mL) of (R)-(+)- 2,2-dimethyl-1,3-dioxolane-4-carboxaldehyde (0.34 g, 2.6 mmol), prepared as described in Jackson, Synthetic Commun. 1988, 18(4), 337–341) was added. The resulting solution was stirred for 30 minutes at −78° C., and the cooling bath was removed. The reaction was stirred for 1 hour and then quenched with excess saturated aqueous $NH_4Cl$. The mixture was partitioned between saturated aqueous $NH_4Cl$ and ethyl acetate. The organic layer was washed twice with brine, dried over $MgSO_4$, filtered, and concentrated in vacuo to provide a cloudy oil which was purified by chromatography on silica gel (20% ether:hexanes) to give the less polar anti-(4R, 1'S) alcohol (0.193 g, 20%), a mixture of both isomers (0.233 g, 23%), and the more polar syn-(4R, I'R) alcohol (0.149 g, 15%).

Step 2: syn-(4R, 1'R)- and anti-(4R, 1'S)-2,2-dimethyl-4-[(5-fluoro-3 -(napth-2-ylmethyloxy)phenyl)methyloxymethyl[- 1,3-dioxolane.

Each alcohol isomer prepared in step 1 was independently methylated following the procedure described for the anti-isomer. A flask was charged with anhydrous DMF (5 mL) and(4R, 1'S)-2,2-dimethyl-4-2,2-dimethyl-[(5-fluoro-3-(napth- 2-ylmethyloxy)phenyl)hydroxymethyl]-1,3-dioxolane (0.185 g, 0.484 mmol). Sodium hydride (80% oil dispersion, 14.5 mg, 0.484 mmol) was added in a single portion and the reaction mixture was stirred at ambient temperature until gas evolution ceased (5–10 minutes). To the resulting solution was added methyl iodide (103 μL, 0.726 mmol; freshly filtered through a neutral alumina pad) and the reaction mixture was stirred at ambient temperature for 0.5 hours. The reaction was quenched by adding water and was then partitioned between water and ethyl acetate. The organic layer was washed twice with brine, dried over $MgSO_4$, filtered, and concentrated in vacuo to provide a yellow oil which was purified by chromatography on silica gel (50% ether:hexanes) to give anti-(4R, 1'S)-2,2-dimethyl-4-2,2-dimethyl[ (5-fluoro-3-(napth-2-ylmethyloxy)phenyl)methyloxymethyl ]-1,3-dioxolane (0.176 g, 92%) as a colorless oil. $^1H$ NMR (300 MHz, $CDCl_3$) δ 7.83–7.90 (4H, m), 7.47–7.55 (3H, m), 6.79 (1H, br s), 6.63–6.72 (2H, m), 5.22 (2H, s), ca. 4.12 (1H, m), 4.0–4.05 (3H, m), 3.35 (3H, s), 1.41 (3H, s), 1.29 (3H, s). MS m/e 397 (M+H) $^+$, 414 $(M+NH_4)^+$. Analysis calc'd for $C_{24}H_{25}O_4F(0.1\ H_2O)$: C, 72.38; H, 6.38. Found: C, 72.14; H, 6.05.

Methylation of (4R, 1'R)-2,2-dimethyl-4-2,2-dimethyl-[(5-fluoro-3-(napth-2as ylmethyloxy)phenyl)hydroxymethyl]-1,3-dioxolane as described above gave syn( 4R, 1'R)-2,2-dimethyl-4-2,2-dimethyl-[(5-fluoro-3 -(napth-2-ylmethyloxy)phenyl)methyloxymethyl] -1,3-dioxolane. $^1H$ NMR (300 MHz, $CDCl_3$) δ7.83–7.90 (4H, m), 7.47–7.55 (3H, m), 6.78 (1H, br s), 6.63–6.72 (2H, m), 5.22 (2H, s), 4.24 (1H, quartet, J= 7.5 Hz), 4.08 (1 H, d, J= 7.5 Hz), 3.60 (1H, dd, J= 8.5, 7.5 Hz), 3.52 (1H, dd, J= 8.0, 7.5 Hz), 3.25 (3H, s), 1.42 (3H, s), 1.37 (3H, s). MS m/e 397 $(M+H)^+$, 414 $(M+NH_4)^+$. Analysis calc'd for $C_{24}H_{25}O_4F(0.75\ H_2O)$: C, 70.31; H, 6.15. Found: C, 70.31; H, 5.94.

Step 3: anti-(1S, 2R)-2,3-dihydroxy-1 -methyloxymethyl-1-(5-fluoro-3-(napth-2-ylmethyloxy)phenyl)propane.

To a solution of anti-(4R, 1'S)-2,2-dimethyl-4-[ (5-fluoro-3-(napth-2ylmethyloxy)phenyl)methyloxymethyl] -1,3-dioxolane (0.145 g, 0.37 mmol), prepared as in step 2, dissolved in methanol (10 mL) was added catalytic para-toluenesulfonic acid monohydrate (25 mg, 0.13 mmol). The reaction was stirred at ambient temperature until TLC indicated complete reaction (~18 hours). The is volatiles were removed in vacuo and the resulting solution was partitioned between ethyl acetate and saturated aqueous $NaHCO_3$. The organic phase was washed twice with brine, dried over $MgSO_4$, filtered and concentrated in vacuo to provide anti-(1 S, 2R) 2,3-dihydroxy-1-methyloxymethyl-1 -(5-fluoro-3-

(napth-2-ylmethyloxy)phenyl)propane as a colorless solid (120 mg, 92%) which was carried on without further purification.

Step 4: anti-(1S, 2R)-1-[(5-fluoro-3-(napth-2-ylmethyloxy)-1,2,3-trimethoxypropane.

To a solution in dry THF (5 mL) of anti-(1S, 2R)-2,3-dihydroxy-1 -[(5-fluoro- 3-(napth-2-ylmethyloxy)phenyl)]-1-methoxypropane (50 mg, 0.14 mmol), prepared as in Example 2, step 1, was added sodium hydride (8.4 mg; 80% oil dispersion; 0.28 mmol) was. After gas evolution ceased, methyl iodide (17 μL; 0.28 mmol) was added and the reaction was stirred at ambient temperature for 15 hours. Excess sodium hydride was quenched by careful addition of water. The reaction was partitioned between water and ethyl acetate. The aqueous layer was extracted twice with ethyl acetate. The combined organic layers were washed with brine, dried over $MgSO_4$, filtered, and concentrated in vacuo to provide an orange oil. Purification by slica gel chromatography (ethyl acetate/hexanes) provided pure anti-(1 S, 2R)-1-[(5-fluoro- 3-((napth-2-yl)methoxy)-phenyl) ]-1,2,3-trimethoxypropane (40 mg, 74% ). $^1H$ NMR (300 MHz, $CDCl_3$) δ7.83–7.90 (4H, m), 7.47–7.55 (3H, m), 6.82 (1H, br s), 6.65–6.72 (2H, m), 5.22 (2H, s), 4.21 (1H, d, J= 6 Hz), 3.47–3.53 (2H, m), 3.34–3.42 (1H, m), 3.34 (3H, s), 3.27 (3H, s), 3.25 (3H, s). MS m/e 402 $(M+NH_4)^+$. Analysis calc'd for $C_{23}H_{25}O_4F$: C, 71.86; H, 6.55. Found: C, 71.61; H, 6.52.

Step 5: anti-(1S, 2R)-1-[(5-fluoro-3-hydroxyphenyl)]-1,2,3-trimethoxypropane.

The desired compound was prepared according to the method of Example 1, step 4, except substituting anti-(1S, 2R)-1-[(5-fluoro-3-((napth-2-yl)methoxy)phenyl)] -1,2,3-trimethoxypropane, prepared as in step 4, for E-(4S)-O-methyl-2,2dimethyl -4–2,2-dimethyl-[(5-fluoro-3-(napth-2-ylmethoxy)phenyl)oximinomethyl ]- 1,3-dioxolane.

Step 6: anti-(1S, 2R)-1-[(5-fluoro-3-(4-(N', N'-dimethylaminocarbonyl-N-methylamino)-benzyloxy)phenyl)] -1,2,3-trimethoxypropane.

The desired compound was prepared according to the method of Example 1, step 9, except substituting anti-(1S, 2R)-1-[(5-fluoro-3-hydroxyphenyl)]-1,2,3-trimethoxypropane, prepared as in step 5, for E-(4S)-O-methyl-2,2-dimethyl-4–2,2-dimethyl-[ (5-fluoro-3-hydroxyphen-1-yl)oximinomethyl ]-1,3-dioxolane. Purification by chromatography on silica gel (50% ethyl acetate:hexanes) provided anti-(1S, 2R)- 1-[(5-fluoro-3-(4 -(N', N'-dimethylaminocarbonyl-N-methylamino)benzyloxy)phenyl)] -1,2, 3-trimethoxypropane. $^1$H NMR (300 MHz, $CDCl_3$) δ7.48 (2H, d, J= 9 Hz), 7.07 (2H, d, J= 9 Hz), 6.87 (1H, br s), 6.69 (1H, br d, J= 9.5 Hz), 6.62 (1H, dr, J= 10.5, 3 Hz), 5.01 (2H, s), 4.20 (1H, d, J =6 Hz), 3.48–3.52 (2H, m), 3.37–3.42 (1H, m), 3.37 (3H, s), 3.27 (3H, s) (3H, s), 3.22 (3H, s). MS m/e 435 $(M+H)^+$, 452 $(M+NH_4)$. Analysis calc'd for $C_{23}H_{31}N_2O_5F$: C, 63.57; H, 7.19; N, 6.44. Found: C, 63.41; H, 7.28; N, 6.28.

EXAMPLE 15

Preparation of anti-(1S, 2R)-1-[(5-fluoro-3-{4-(N-acetyl-N-methylamino): benzyloxy)phenyl)]-1,2,3-trimethoxypropane.

The desired compound (yellow oil, 154 mg, 91%), was prepared according to the method of Example 2, step 4, except substituting anti-(1S, 2R)-1-[(5-fluoro-3-hydroxyphenyl)] -1,2,3-trimethoxypropane, prepared as in Example 8, step 5, for E-( 4S)-O-methyl-2,2-dimethyl-4–2, 2-dimethyl-[(5-fluoro-3-hydroxyphenyl)oximinomethyl] -1,3-dioxolane. 1H NMR (300 MHz, $CDCl_3$) δ7.49 (2H, d, J= 9 Hz), 7.22 (2H, d, J= 9 Hz), 6.79 (1H, br s), 6.72 (1H, br d, J= 9.5 Hz), 6.64 (1H, dr, J= 10.5, 3 Hz), 5.07 (2H, s); 4.21 (1H, d, J= 6 Hz), 3.49–3.53 (2 3.37–3.42 (1H, m), 3.37 (3H, s), 3.28 (6H, s), 3.26 (3H, s), 1.89 (3H, br s) m/e 406 $(M+H)^+$, 423 $(M+NH_4)^+$. Analysis calc'd for $C_{22}H_{28} NO_5F$: C, 65.17; H, 6.96; N, 3.45. Found: C, 65.17; H, 7.09; N, 3.27.

EXAMPLE 16

Preparation of anti-(1S, 2R)-1-[3-(4-(N-allyl-N-methylamino) phenylthioxyl)phenyl]: 1,2,3 -trimethoxypropane.

The desired compound is prepared according to the method of Example 14, steps 2–4, except substituting (4R, 1'R) and (4R, 1'S)-2,2-dimethyl-4-[(3-(4-(N allyl-N-methylamino)phenylthioxyl)phenyl)hydroxymethyl]-1,3-dioxolane, prepared as in Example 3, step 6, for (4R, 1'S)-2,2-dimethyl-4–2,2-dimethyl-[(5-fluoro-3-( napth-2-ylmethyloxy)phenyl)hydroxymethyl]-1,3-dioxolane.

EXAMPLE 17

Preparation of anti-(1S, 2R)-1-[3-(4-(N',N'-dimethylaminocarbonyl-N-methylamino)phenylthioxyl) phenyl]-1,2,3-trimethoxypropane.

The desired compound is prepared according to the method of Example 4, except substituting anti-(1S, 2R)-1-[3-(4-(N-allyl-N-methylamino)phenylthioxyl)phenyl] -1,2, 3-trimethoxypropane, prepared as in Example 15, for Z-(4S)-O-methyl-2,2-dimethyl-4-[(3-(4 -(N-allyl-N-methylamino)phenylthioxyl)phenyl)oximinomethyl]-1,3-dioxolane.

EXAMPLE 18

Preparation of anti-(1S, 2R)-1-[5-fluoro-3-(4-(N', N' -dimethylaminocarbonyl-N-methylamino)benzylthioxyl)phenyl] -1,2,3-trimethoxypropane.

Step 1: anti-(1S, 2R)-1-[(5-fluoro-3-(benzylthioxy)phenyl-1,2,3: trimethoxypropane.

The desired compound is prepared according to the method of Example 14, steps 1–4, except substituting 5-fluoro-3-benzylthiobromobenzene, prepared as described in EPA 420 511 (Example 4), for 3-(napth-2-ylmethyloxy)-5-fluorobromobenzene.

Step 2: anti-(1S, 2R)-1-[(5-fluoro-3-mercaptophenyl) ]-1,2, 3-trimethoxypropane.

The desired compound is prepared according to the method of Example 13, step 2, except substituting anti-(1S, 2R)-1-[(5-fluoro-3-(benzylthioxy)phenyl)]- 1,2,3-trimethoxypropane, prepared as in step 1, for Z- and E-(4S)-O-methyl-2,2-dimethyl- 4-[(5-fluoro-3-(benzylthioxy)phenyl)oximinomethyl ]-1,3-dioxolane.

Step 3: anti-(1S, 2R)-1-[5-fluoro-3-(4-(N', N'-dimethylaminocarbonyl-N-methylamino) benzylthioxyl)phenyl]-1,2, 3-trimethoxypropane.

The desired compound is prepared according to the method of Example 14, step 6, except substituting anti-(1S, 2R)-1-[(5-fluoro-3-mercaptophenyl)]-1,2,3trimethoxypropane prepared as in step 2, for anti-(1S, 2R)-1-[(5-fluoro-3-hydroxyphenyl) ]-1,2,3-trimethoxypropane.

EXAMPLE 19

Preparation of Z- and E-(4S)-O-methyl-2,2-dimethyl-4-[(5-fluoro-3 -((4-(N', N'-dimethylaminocarbonyl-N-methylamino)methyl)benzyloxy)phenyl)oximinomethyl]- 1,3-dioxolane.

Step 1: Z- and E-(4S)-O-methyl-2,2-dimethyl-4-[(5-fluoro-3 -(4: bromomethyl)benzyloxy)phenyl)oximinomethyl]-1, 3-dioxolane.

The desired compounds are prepared according to the method of Example 1, step 9, except substituting α,α'-dibromo-p-xylene for 4 -(N',N'-dimethylaminocarbonyl-N-methylamino)benzyl chloride.

Step 2: Z- and E-(4S)-O-methyl-2,2-dimethyl-4-[(5-fluoro-3 -((4-(N', N'dimethylaminocarbonylamino)methyl)benzyloxy) phenyl)oximinomethyl ]-1,3-dioxolane.

The desired compounds are prepared by reaction of a solution of 1,1-dimethylurea in DMF with NaH and Z- and E-(4S)-O-methyl-2,2-dimethyl-4–2,2-dimethyl-[ (5-fluoro-3-(4-bromomethyl)benzyloxy)phenyl)oximinomethyl ]-1,3-dioxolane, which is prepared as described in step 1.

Step 3: Z- and E-(4S)-O-methyl.-.2.2-dimethyl-4-[(5-fluoro-3-((4-(N', N': a0 dimethylaminocarbonyl-N-methylamino)methyl)benzyloxy)phenyl)oximinomethyl]: 1,3-dioxolane.

The desired compounds are prepared according to the method of Example 14, step 2, except substituting Z- and E-(4S)-O-methyl-2,2-dimethyl-4-[(5-fluoro-3-((4( N', N'-dimethylaminocarbonylamino)methyl)benzyloxy)phenyl )oximinomethyl ]-1,3-dioxolane, prepared as in step 2, for (4R, 1'S)-2,2-dimethyl-4-[(5-fluoro-3-(napth-2-ylmethyloxy) phenyl)hydroxymethyl]-1,3-dioxolane.

EXAMPLE 20

Preparation of Z- and E-(4S)-O-methyl-2,2-dimethyl-4-[ (5-fluoro-3-((4-imidazolidin-2-on-1-ylmethyl)benzyloxy)phenyl)oximinomethyl]-1,3-dioxolane.

The desired compounds are prepared according to the method of Example 19, step 2, except substituting 2-imidazolidinone for 1,1-dimethylurea.

EXAMPLE 21

Preparation of Z- and E-(IS)-O-methyl-4-[(3-(4-(N-allyl-N-methylamino) phenylthioxyl)phenyl)oximinomethyl] ]-1,2-dimethoxyethane.

The desired compounds are prepared according to the method of Example 14, steps 3 and 4, except substituting Z- and E-(4S)-O-Methyl-2,2-dimethyl-4 -[(3-(4-(N-allyl-N-methylamino) phenylthioxyl)phenyl)oximinomethyl]-1,3-dioxolane, prepared as in Example 3, for anti-(4R, 1'S)-2,2 -dimethyl-4-[(5-fluoro-3-(napth-2-ylmethyloxy)phenyl)m -1,3-dioxolane.

EXAMPLE 22

Preparation of Z- and E-(1S)-O-methyl-4-[(3(4-(N', N'-dimethylaminocarbonyl-N-methylamino) phenylthioxyl)phenyl)oximinomethyl]-1,2-dimethoxyethane.

The desired compounds are prepared according to the method of Example 4, except substituting Z- and E-(1S)-O-methyl-4-[(3-(4-(N-allyl-N-methylamino)phenylthioxy-1)phenyl)oximinomethyl]]-1,2-dimethoxyethane, prepared as in Example 21, for Z-(4S)-O-methyl-2,2-dimethyl-4-[(3-(4 -(N-allyl-N-methylamino)phenylthioxyl)phenyl)oximinomethyl] -1,3-dioxolane.

EXAMPLE 23

Preparation of Z- and E-(4S)-O-methyl-2,2-dimethyl-4-[(3-(4-(N-acetyl-N-methylamino) phenylthioxyl)phenyl)oximinomethyl]-1,3-dioxolane.

The desired compounds are prepared according to the method of Example 1, step 9, except substituting acetyl chloride for N, N-dimethylcarbamoyl chloride.

EXAMPLE 24

Preparation of E- and Z-(4S)-O-methyl-2,2-dimethyl-4 -[(5-fluoro-3-(4-(N-allyl-N-methylamino) phenylthioxyl) 1,3-dioxolane.

The desired compounds are prepared according to the method of Example 3, except substituting 5-fluoro-3-bromobenzenethiol, prepared according to the method described in EPA 420 511 (Example 4), for m-bromobenzenethiol.

EXAMPLE 25

Preparation of E- and Z-(4S)-O-methyl-2,2-dimethyl-4-[ (5-fluoro-3 -(4-(N', N'-dimethylaminocarbonyl-N-methylamino) phenylthioxyl)phenyl)oximinomethyl]-1,3: dioxolane.

The desired compounds are prepared according to the method of Example 4, except substituting Z-(4S)-O-methyl-2,2-dimethyl-4-[ (5- fluoro-3-(4-(N-allyl-N-methylamino)phenylthioxyl)phenyl)oximinomethyl]-1,3-dioxolane, prepared as in Example 24, for Z-(4S)-O-methyl-2,2-dimethyl-4-[(3-(4-(N-allyl-N-methylamino)phenyl thioxyl )phenyl)oximinomethyl ]-1,3-dioxolane.

EXAMPLE 26

Preparation of anti-(1S, 2R)-1- [5-fluoro-3 -(4-(N-allyl-N-methylamino)phenylthioxyl)phenyl]-1,2,3-trimethoxypropane.

The desired compound is prepared according to the method of Example 16, except substituting (4R, 1'R) and (4R, 1'S)-2,2 -dimethyl-4-[(5-fluoro-3 -(4-(N-allyl-N-methylamino)phenylthioxyl)phenyl)hydroxymethyl] -1,3-dioxolane, prepared as in Example 24, for (4R, 1'S)-2,2 -dimethyl-4-2,2-dimethyl-[(5-fluoro-3-(napth-2-ylmethyloxy -1,3-dioxolane.

EXAMPLE 27

Preparation of anti-(1 S, 2R)-1-[5-fluoro-3-(4-(N', N'-dimethylaminocarbonyl-N-methylamino) phenylthioxyl)phenyl]-1,2,3-trimethoxypropane.

The desired compound is prepared according to the method of Example 17, except substituting anti-(1S, 2R)-1-[5-fluoro-3-(4-(N-allyl-N-methylamino)phenylthioxyl)phenyl] -1,2,3-trimethoxypropane, prepared as in Example 26, for anti-(1S, 2R)-1-[3-(4-(N-allyl-N-methylamino)phenylthioxyl)phenyl] -1,2,3-trimethoxypropane.

EXAMPLE 28

Preparation of E- and Z-(4S)-O-methyl-2,2-dimethyl-4-[(3 -(4-methylpiperazin-1-ylcarbonyl)-N-methylamino) phenylthioxyl)phenyl)oximinomethyl]- 1,3-dioxolane.

The desired compounds are prepared by treatment of E- and Z-(4S)-O-methyl-2,2 -dimethyl-4-[(3-(4-N-methylaminophenylthioxyl)phenyl)oximinomethyl]-1,3-dioxolane, prepared as in Example 4, step 1, with triphosgene and 4-methylpiperazine according to the method of Eckert, H., and Forster, B., *Angew. Chem. Int. Ed.*, 1987, 26(9), 894–895.

Example 29

Preparation of anti-(1S, 2R)-1-[3-(4-(N-(4-methylpiperazin-1-ylcarbonyl)-N-methylamino) phenylthioxyl)phenyl]-1,2,3-trimethoxypropane.

The desired compound is prepared according to the method of Example 28, except substituting anti-(1S, 2R)-1-[3-(4-(N-methylamino)phenylthioxyl)phenyl]- 1,2,3-trimethoxypropane, prepared as in Example 16, for E- and Z-(4S)-O-methyl 2,2-dimethyl-4-[(3-(4-N-methylaminophenylthioxyl)phenyl)oximinomethyl]-1,3-dioxolane.

The compounds represented in Table 2 are prepared as described in Schemes 4 and 5 and Example 28.

TABLE 2

Novel 1,3-dioxolane inhibitors of 5-Lipoxygenase.

| Example | $R^5$ | $R^1$ | $R^9$ | $R^{10}$ |
|---|---|---|---|---|
| 30 | H | Me | Me | Br-CH₂CH₂CH₂CH₂- |
| 31 | F | Me | Me | Br-CH₂CH₂CH₂CH₂- |
| 32 | H | Me | Me | H₂N-CH₂CH₂CH₂CH₂- |
| 33 | F | Me | Me | H₂N-CH₂CH₂CH₂CH₂- |
| 34 | H | Me | Me | HO-(CH₂)₅- |
| 35 | F | Me | Me | HO-(CH₂)₅- |
| 36 | H | Me | Me | HO-C(=O)-(CH₂)₃- |
| 37 | F | Me | Me | HO-C(=O)-(CH₂)₃- |
| 38 | H | Me | Me | EtO-C(=O)-(CH₂)₃- |
| 39 | F | Me | Me | EtO-C(=O)-(CH₂)₃- |
| 40 | H | Me | Me | CH₃-NH-C(=O)-(CH₂)₃- |
| 41 | F | Me | Me | CH₃-NH-C(=O)-(CH₂)₃- |
| 42 | H | Me | — | morpholinyl |
| 43 | F | Me | — | morpholinyl |
| 44 | H | Me | — | thiomorpholinyl |
| 45 | F | Me | — | thiomorpholinyl |
| 46 | H | Me | — | piperidinyl |
| 47 | F | Me | — | piperidinyl |

The compounds represented in Table 3 are prepared as described in Schemes 4 and 5 and Example 29.

TABLE 3

Novel Trimethoxypropane inhibitors of 5-Lipoxygenase.

| Example | $R^5$ | $R^1$ | $R^9$ | $R^{10}$ |
|---|---|---|---|---|
| 48 | H | Me | Me | Br~~~ |
| 49 | F | Me | Me | Br~~~ |
| 50 | H | Me | Me | H₂N~~~ |
| 51 | F | Me | Me | H₂N~~~ |
| 52 | H | Me | Me | HO~~~ |
| 53 | F | Me | Me | HO~~~ |
| 54 | H | Me | Me | HO-C(O)-~~ |
| 55 | F | Me | Me | HO-C(O)-~~ |
| 56 | H | Me | Me | EtO-C(O)-~~ |
| 57 | F | Me | Me | EtO-C(O)-~~ |
| 58 | H | Me | Me | CH₃-NH-C(O)-~~ |
| 59 | F | Me | Me | CH₃-NH-C(O)-~~ |
| 60 | H | Me |   | morpholino (O,N) |
| 61 | F | Me |   | morpholino (O,N) |
| 62 | H | Me |   | thiomorpholino (S,O) |
| 63 | F | Me |   | thiomorpholino (S,O) |
| 64 | H | Me |   | piperidino |
| 65 | F | Me |   | piperidino |

We claim:

1. A compound having the structure

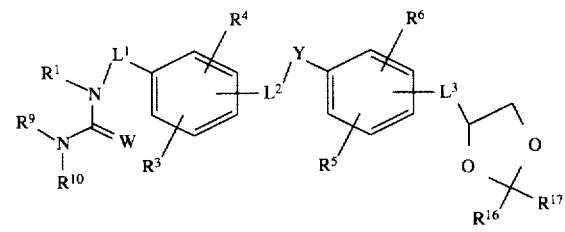

or a pharmaceutically acceptable salt thereof where
$L^1$ and $L^2$ are independently a single bond or alkylene of one to three carbon atoms;
$L^3$ is $$\underset{}{\overset{N-OR^{15}}{\parallel}}$$

where
$R^{15}$ is hydrogen or alkyl of one to four carbon atoms;
Y is selected from oxygen and >S(O)n where n= 0, 1, or 2;
$R^1$ is alkyl of one to four carbon atoms;
W is oxygen or sulfur;
$R^9$ is alkyl of one to four carbon atoms;
$R^{10}$ is selected from the group consisting of
  (a) hydrogen,
  (b) alkyl of one to four carbon atoms,
  (c) haloalkyl of one to four carbon atoms,
  (d) cyanoalkyl of one to four carbon atoms,
  (e) unsubstituted phenyl,
  (f) phenyl substituted with a substituent selected from the group consisting of alkyl of one to four carbon atoms, alkoxy of one to four carbon atoms, haloalkyl of one to four carbon atoms, and halogen,
  (g) hydroxyalkyl of one to four carbon atoms,
  (h) aminoalkyl of one to four carbon atoms,
  (i) carboxyalkyl of one to four carbon atoms, and
  (j) (alkoxycarbonyl)alkyl where the alkyl and alkoxy portions are independently of one to four carbon atoms;

$R^3$, $R^4$, $R^5$, and $R^6$ are independently selected from the group consisting of hydrogen, alkyl of one to four carbon atoms, alkoxy of one to four carbon atoms, haloalkyl of one to four carbon atoms, halogen, cyano, amino, alkoxycarbonyl of one to four carbon atoms, and dialkylaminocarbonyl where the alkyl portions are each of one to four carbon atoms; and $R^{16}$ and $R^{17}$ are independently selected from the group consisting of hydrogen, alkyl of one to four carbon atoms, alkoxy of one to four carbon atoms, and haloalkyl of one to four carbon atoms.

2. A compound or pharmaceutically acceptable salt thereof as defined by claim 1 wherein $L^1$ is a single bond.

3. A compound or pharmaceutically acceptable salt thereof as defined by claim 2 wherein $L^2$ is a single bond or methylene.

4. A compound or pharmaceutically acceptable salt thereof as defined by claim 2 wherein $L^2$ is a valence bond;

$L^3$ is

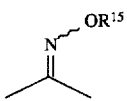

wherein $R^{15}$ is hydrogen or alkyl of one to four carbon atoms; and

Y is $>S(O)_n$ where n= 0, 1, or 2.

5. A compound or pharmaceutically acceptable salt thereof as defined by claim 4 having the structure

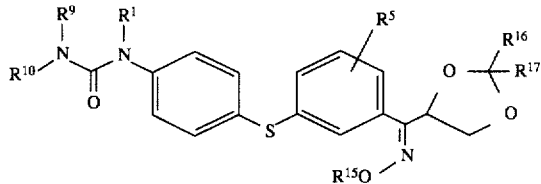

wherein $R^1$, $R^9$, and $R^{10}$ are alkyl of one to four carbon atoms, $R^5$ is hydrogen or halogen, and $R^{15}$ is hydrogen or alkyl of one to four carbon atoms.

6. A compound or pharmaceutically acceptable salt thereof as defined by claim 2 wherein $L^2$ is a single bond;

$L^3$ is

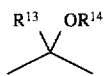

wherein $R^{13}$ hydrogen, and $R^{14}$ is alkyl of one to four carbon atoms;

and

Y is $>S(O)_n$ where n=0, 1, or 2.

7. A compound or pharmaceutically acceptable salt thereof as defined by claim 1 having the structure

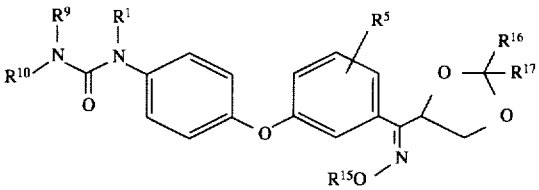

wherein $R^1$, $R^9$, and $R^{10}$ are alkyl of one to four carbon atoms, $R^5$ is hydrogen or halogen, and $R^{15}$, $R^{16}$ and $R^{17}$ are hydrogen or alkyl of one to four carbon atoms.

8. A compound or pharmaceutically acceptable salt thereof as defined by claim 1 selected from the group consisting of:

E-(4S)-O-methyl-2,2-dimethyl-4-[ (5-fluoro-3 -(4-(N', N'-dimethyaminocarbonyl-N-methylamino)benzyloxy)phenyl)oximinomethyl] -1,3-dioxolane, Z-(4S )-O-methyl-2,2-dimethyl-4-[(3-(4-(N', N'-dimethylaminocarbonyl-N-methylamino) phenylthioxyl)phenyl)oximinomethyl]-1,3-dioxolane, E-(4S )-O-methyl-2,2-dimethyl-4-[(3-(4-(N', N'-dimethylaminocarbonyl-N-methylamino)phenylthioxy) -1,3-dioxolane, E-(4R)-O-methyl-2,2-dimethyl-4-[(5-fluoro-3-(4 -(N', N'-dimethylaminocarbon-yl-N-methylamino)benzyloxy)phenyl)oximinomethyl] -1,3-dioxolane.

9. A pharmaceutical composition for inhibiting the biosynthesis of leukotrienes comprising a therapeutically effective amount of a compound as defined by claim 1 in combination with a pharmaceutically acceptable carrier.

10. A method of inhibiting the biosynthesis of leukotrienes comprising administering to a mammal in need of such treatment a therapeutically effective amount of a compound as defined by claim 1.

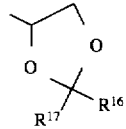

* * * * *

UNITED STATES PATENT AND TRADEMARK OFFICE
CERTIFICATE OF CORRECTION

PATENT NO. : 5,516,795
DATED : May, 14, 1996
INVENTOR(S) : L. Chernesky and J. F. Dellaria It is certified that error appears in the above-indentified patent and that said Letters Patent is hereby corrected as shown below:

Column 41, line 20, change "tour" to --four--.

Column 41, line 31, change "valence" to --single--.

Column 42, line 38-39, change "phenylthioxy)-1,3-dioxane," to --phenylthioxyl)phenyl)oximinomethyl]-1,3-dioxane,--.

Column 42, line 41, change "dimethylaminocarbon-yl" to --dimethylaminocarbonyl--.

Column 42, line 51-56, delete the structural formula therein.

Signed and Sealed this

Tenth Day of December, 199

Attest:

BRUCE LEHMAN

*Attesting Officer*     *Commissioner of Patents and Trademarks*